(12) United States Patent
Burns et al.

(10) Patent No.: US 7,662,999 B2
(45) Date of Patent: Feb. 16, 2010

(54) RECOGNITION OF OLIGOSACCHARIDE MOLECULAR TARGETS BY POLYCATIONIC SMALL MOLECULE INHIBITORS AND TREATMENT OF IMMUNOLOGICAL DISORDERS AND INFECTIOUS DISEASES

(75) Inventors: Mark R. Burns, Kenmore, WA (US); Sunil A. David, Lawrence, KS (US)

(73) Assignees: National Institutes of Health (NIH), Bethesda, MD (US); The United States of America as represented by the Department of Health and Human Services (DHHS), Washington, DC (US); U.S. Government NIH Division of Extramural Inventions and Technology Resources (DEITR)

( * ) Notice: Subject to any disclaimer, the term of this patent is extended or adjusted under 35 U.S.C. 154(b) by 0 days.

(21) Appl. No.: 11/693,941

(22) Filed: Mar. 30, 2007

(65) Prior Publication Data
US 2007/0232674 A1    Oct. 4, 2007

Related U.S. Application Data

(62) Division of application No. 11/254,743, filed on Oct. 21, 2005, now Pat. No. 7,199,267.

(51) Int. Cl.
*C07C 233/01* (2006.01)
(52) U.S. Cl. .................................... 564/152
(58) Field of Classification Search .............. None
See application file for complete search history.

(56) References Cited

U.S. PATENT DOCUMENTS

| 5,998,482 | A  * | 12/1999 | David et al. | 514/626 |
|---|---|---|---|---|
| 6,646,149 | B1 * | 11/2003 | Vermeulin et al. | 560/25 |
| 6,872,852 | B2 * | 3/2005 | Burns | 564/306 |
| 6,919,483 | B2 * | 7/2005 | Burns et al. | 564/453 |
| 7,160,923 | B1 * | 1/2007 | Vermeulin et al. | 514/626 |
| 7,208,528 | B1 * | 4/2007 | Vermeulin et al. | 514/626 |
| 7,388,112 | B2 * | 6/2008 | Burns et al. | 564/453 |
| 7,411,002 | B2 * | 8/2008 | Burns et al. | 514/601 |
| 7,432,302 | B2 * | 10/2008 | Burns et al. | 514/616 |

OTHER PUBLICATIONS

Cirioni et al. "Single-Dose Intraperitoneal Magainins Improve Survival in a Gram-Negative-Pathogen Septic Shock Rat Model" Antimicrobial Agents and Chemotherapy, 2002, 46, 101-104.*

Opal "The host response to endotoxin, antilipopolysaccharide strategies, and the management of severe sepsis," International Journal of Medical Microbiology, 2007, 297, 365-377.*

* cited by examiner

*Primary Examiner*—Cecilia Tsang
*Assistant Examiner*—Christina Bradley
(74) *Attorney, Agent, or Firm*—Connolly Bove Lodge & Hutz LLP

(57) ABSTRACT

Small molecule polycationic agents are used to modulate or interrupt biological processes by binding to oligosaccharide-based biomolecules. Compounds that inhibit nitric oxide, TNFα or other immunomodulators are provided and are useful for treating immunological disease and disease of an infectious disorder.

7 Claims, 5 Drawing Sheets
(2 of 5 Drawing Sheet(s) Filed in Color)

Figure 2: *Top panel:* Histogram of relative binding affinities ($IC_{50}$) of the entire library, showing a distinct biphasic distribution of high- (green Gaussian fit curve) and low-affinity binders (red curve). Vector analysis of components in the high affinity ($ED_{50} < 10$ μM; n=52) analogs (*bottom left*), and weak-binding compounds (n=488) (*bottom right*). PORTION 1 and 2 monomers correspond exactly to the elements in Chart 1. PORTION 3 elements: 1-5: Gly (3.A) series; 6-10: β-Ala (3.B) series; 11-15: GABA (3.C) series in Chart 1. Thus, for PORTION 3 in the bottom panel, elements 2, 7, and 12 correspond to the $C_{18}$-Gly, $C_{18}$-β-Ala, and $C_{18}$-GABA, respectively.

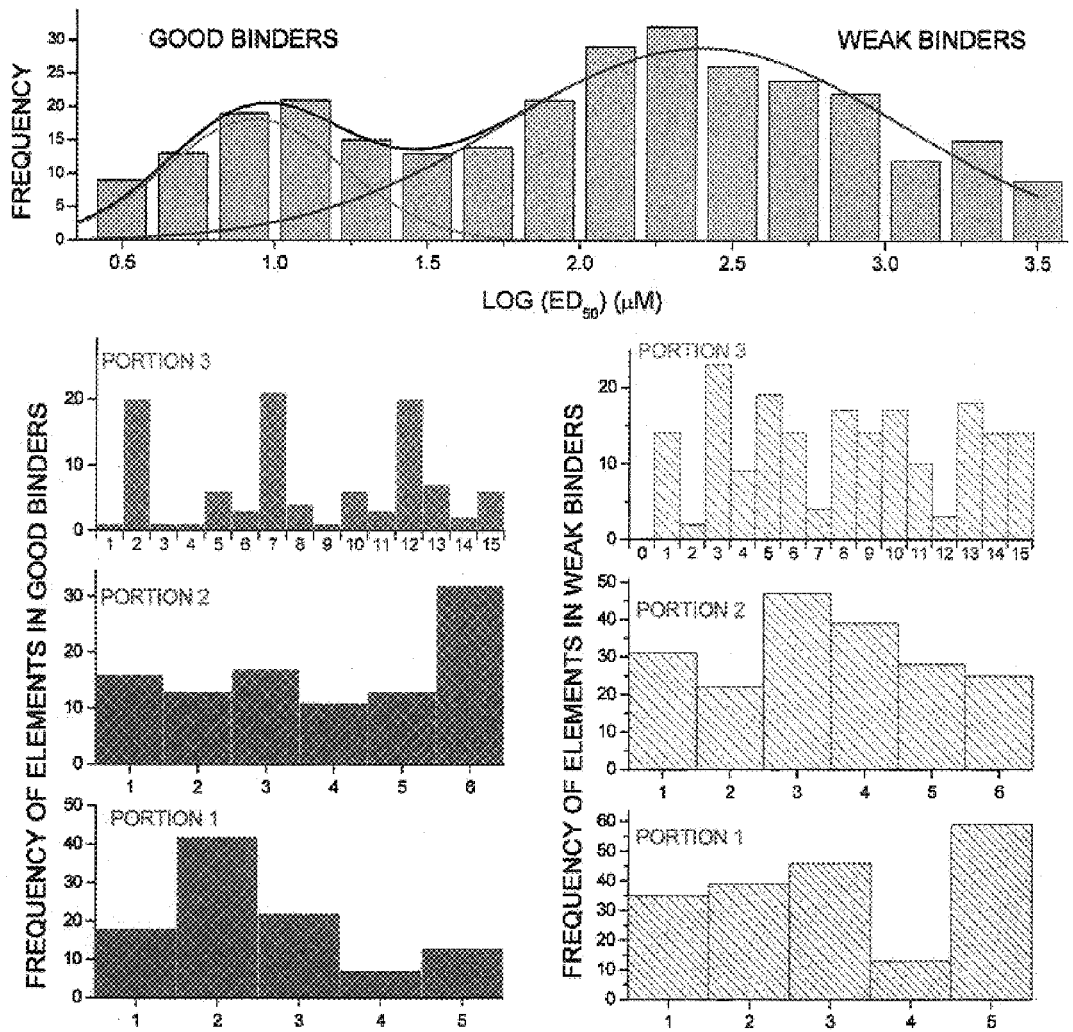

Figure 4: Representative data for inhibition of nitric oxide production (measured as nitrite) in murine macrophage J774A.1 cells stimulated with 100 ng/ml LPS and graded concentrations of test compounds. $IC_{50}$ values (listed in Table 1) were computed from curve-fits using a four-parameter logistic equation.

RECOGNITION OF OLIGOSACCHARIDE MOLECULAR TARGETS BY POLYCATIONIC SMALL MOLECULE INHIBITORS AND TREATMENT OF IMMUNOLOGICAL DISORDERS AND INFECTIOUS DISEASES

CROSS-REFERENCE TO RELATED APPLICATION

This application is a Divisional U.S. application Ser. No. 11/254,743, now U.S. Pat. No. 7,199,267 filed Oct. 21, 2005.

TECHNICAL FIELD

The present disclosure relates to certain polycationic compounds. The present disclosure also relates to methods and compositions that can be used to define drug targets, setup screening assays and the design of agents to interrupt pathological biological processes involving carbohydrate targets. The present disclosure also relates to drug agents used to treat diseases or conditions, particularly immunological disorders and infectious diseases.

Small molecule polycationic compounds bind and neutralize bacterial lipopolysaccharides, and along with test results suggest their suitability for the prevention or treatment of endotoxic shock states or sepsis.

BACKGROUND

Carbohydrates represent the bulk of organic matter on earth.[1] It has been noted that roughly 80% of secreted and cell-surface proteins are glycosylated.[2] The scientific field of glycobiology involves the investigation of the role that saccharide structure plays in biological function. Given the generally complex structural nature of glycoconjugates, this has been the last of the three major biological materials to be explored in great detail. Unlike proteins and nucleic acids, the biosynthesis of glycosylated biostructures does not involve a templated, message-driven production. A diverse set of enzymes operate on substrates to synthesize three main types of glycoconjugates: 1) N-linked glycoproteins, 2) O-linked glycoproteins and 3) glycosaminoglycans.[3]

The role of oligosaccharides in biological recognition has been amply demonstrated in recent scientific literature. This role extends to cell adhesion, cell-to-cell communications and signal transduction, route to infection by bacteria and viruses, development and immunology.[4] It has been noted that almost all of the key molecules involved in the innate and adaptive immune response are glycoproteins.[5]

The specific biological recognition of saccharides is a tremendous chemical challenge, even for nature, due to their complex, irregular and multifunctional structures.[6] This challenge is made even more difficult by the ability of the polyhydroxylated exteriors to associate well with water. It has been noted that the binding constant for proteins with monosaccharides peak at approximately $10^7$ M$^{-1}$, a remarkable low value for biological molecular recognition.[7] This low molecular affinity for monomeric carbohydrates is magnified biologically through what has become known as the "glycoside cluster effect." This effect is manifested when carbohydrates are oligomerized, thereby maximizing binding efficiencies through not only an additive manner but also through entropic means.[8]

X-ray structures of oligosaccharide-binding proteins have revealed that the polar groups of the carbohydrates are involved in multiple hydrogen bonding interactions with complementary polar donor and acceptor hydrogen bond sites on the protein. Nature has used this complementary interaction to a great extent in order to gain specificity and energy for binding. Furthermore, numerous salt bridges are observed between charged residues on the protein and complementary charged carboxylate, phosphate, sulfate or ammonium functions on the carbohydrate structure. It has been noted that the involvement of serine, tyrosine and threonine hydroxyl groups is relatively uncommon.[9] It has also been noted that most of the complementary non-polar interactions with carbohydrates involve aromatic residues on the protein binding partner.[10] Most of the hydrogen bonds involve planar, multivalent side chain groups (Asn, Asp, Glu, Gln, Arg, His). An additional insight was the recognition of the ability of 2-aminopyridine moiety to act as a heterocyclic mimetic of the asparagines/glutamine amide side chain.[11]

Several examples of the detailed three-dimensional structure of polybasic protein ligands binding to anionic oligosaccharides exist. The binding interaction between fibroblast growth factor and heparin[12] reveals that a significant number of positively charged protein residues interact with the negatively charged glycoconjugate receptor. It is important to recognize that many of the negatively charged species on the receptor are heterogeneously sulfated on alternating L-iduronic and D-glucosamino sugars.[13] X-ray analysis of the glycoprotein hormone follicle-stimulating hormone interacting with its receptor shows that a large buried interface (2600 Å$^2$) with a high charge density (1.13 charges per nm$^2$) defines a universal binding mode where charge complementarity defines specificity.[14] Theoretically, a large energy barrier must be overcome by desolvating the partners before binding can occur.

The carbohydrate-modifying enzymes known as sulfotransferases represent an intriguing method used by nature to reversibly create anionic binding sites on biomolecules. Many literature examples exist of biological phenomena such as development, differentiation and especially immunology which are modulated by the presence or absence of sulfated glyco-conjugates.[15] Specifically, the effects of polyamines on blood coagulation and fibrinolysis in the presence of glycosaminoglycans (GAGs) has been examined because it is known that heparin (HP) interacts with polyamines, especially with spermine.[16]

Recent scientific advances have greatly enabled the ability to delineate the role of specific carbohydrates in biological processes. Reviews of these advances have appeared.[17,18] An especially exciting development is the automated solid-phase synthesis of defined oligosaccharides.[19] The interactions of heparin/heparan sulfate with various proteins have been reviewed.[20] Screening for inhibitors of oligosaccharide-mediated biological events has been successfully applied to the microtiter plate format.[21,22] The use of surface plasmon resonance imaging has been applied to the study of protein-carbohydrate interactions.[23] The general uses of optical biosensors to drug discovery has also been reviewed.[24] Capillary electrophoresis is an additional tool used to define interactions between sulfated polysaccharides and proteins.[25]

Interruption of carbohydrate-mediated disease processes. A report by Joosten et al. showed that a series of dendritic galabiose compounds containing a polyamido core (PAMAM-) had activity in inhibition of bacterial binding in the subnanomolar concentration levels.[26] A report by Yudovin-Farber showed that anti-prion agents could be produced using polycationic oligosaccharides.[27] Furthermore, the elimination of prion particles from infected individuals using polycationic agents has been shown.[28-31] Medicinal chemistry efforts towards inhibition of integrin-mediated events have been made.[32;33] Molecular recognition by these cell adhesive molecules known as integrin receptors on the cell surface is one of the most important biological processes not only in cell adhesion but also in fertilization, organ formation, cell migration, lymphocyte trafficking, immune response, and cancer metastasis.[34] Endotoxins, or lipopolysaccharides (LPS), the predominant structural component of the outer membrane of Gram-negative bacteria,[35-37] play a pivotal role in septic shock, a syndrome of systemic toxicity which occurs frequently when the body's defense mechanisms are compromised or overwhelmed, or as a consequence of antibiotic chemotherapy of serious systemic infections (Gram-negative sepsis).[38-41] Referred to as "blood poisoning" in lay terminology, Gram-negative sepsis is the thirteenth leading cause of overall mortality[42] and the number one cause of deaths in the intensive care unit,[43] accounting for more than 200,000 fatalities in the US annually.[44] Despite tremendous strides in antimicrobial chemotherapy, the incidence of sepsis has risen almost three-fold from 1979 through 2000[45] and sepsis-associated mortality has essentially remained unchanged at about 45%[46], both calling to attention the fact that aggressive antimicrobial therapy alone is insufficient in preventing mortality in patients with serious illnesses, and emphasizing an urgent, unmet need to develop therapeutic options specifically targeting the pathophysiology of sepsis.

The presence of LPS in the systemic circulation causes a widespread activation of the innate immune response[47;48] leading to the uncontrolled production of numerous inflammatory mediators, including tumor necrosis factor-α (TNF-α), interleukin-1β (IL-1β), and interleukin-6 (IL-6), primarily by cells of the monocyte/macrophage lineage,[49;50] as well as others, such as nitric oxide produced by the endothelial cell,[51;52] which, in concert, act to cause a frequently fatal systemic inflammatory response,[53] termed 'septic shock'. The toxic moiety of LPS is its structurally conserved glycolipid component called Lipid A,[54] which is composed of a hydrophilic, bis-phosphorylated diglucosamine backbone, and a hydrophobic domain of 6 (*E. coli*) or 7 (*Salmonella*) acyl chains[54] (FIG. 1). The pharmacophore necessary for the neutralization of lipid A[55] by small molecules requires two protonatable positive charges separated by a distance of ~14 Å, enabling ionic H-bonds between the cationic groups and the lipid A phosphates; in addition, appropriately positioned pendant hydrophobic functionalities are required to further stabilize the resultant complexes via hydrophobic interactions with the polyacyl domain of lipid A (for a recent review, see Ref.[56]). These structural requisites were first identified in certain members of a novel class of compounds, the lipopolyamines, which were originally developed, and are currently being used as DNA transfection (lipofection) reagents.[57-60] In a detailed study of the effect of the hydrocarbon chain length in a homologous series of acylhomospermines, it was shown that $C_{16}$ is the ideal lipophilic substituent, corresponding to maximal affinity, optimal aqueous solubility (and bioavailability), and neutralization potency.[61]

SUMMARY

The present disclosure relates to modulating or interrupting processes which comprises binding oligosaccharide-based biomolecules with small molecule polycationic agents.

The present disclosure also relates to compounds represented by the formulae:

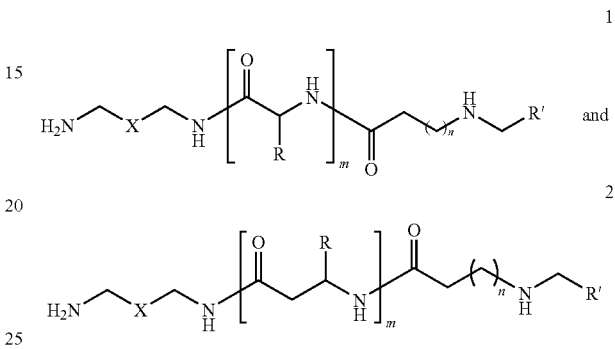

wherein x is selected from the group consisting of —$(CH_2)_y$—; 1,2-$C_6H_4$—; 1,3-$C_6H_4$—; 1,4-$C_6H_4$—; and —$CH_2OCH_2$—;

y is an integer of 0-10;

R is selected from the group consisting of —H, —$CH_3$, —$CH_2C_6H_5$, —$CH_2$-3-indoline, —$CH_2$-2-indoline, and —$CH_2$-4-imidazole m is 0-4;

n is 0-4; and

R' is selected from the group consisting of —$(CH_2)_o$—$CH_3$; —$(CH_2)_o$—$CH_2NH_2$; phenyl; 1-naphthyl and 2-naphthyl;

o is an integer of 0-16;

pharmaceutically acceptable salts thereof; and prodrugs thereof.

The present disclosure also relates to treating diseases of an immunological disorder such as psoriasis, lupus, Crohn's disease, inflammatory bowel disease, rheumatoid arthritis, Type 1 diabetes, Type 2 diabetes or sepsis by administering to a patient in need thereof, an effective amount of a compound disclosed above.

A further aspect of this discloses is concerned with treating diseases of an infectious disorder such as those caused by bacteria, fungi or viruses by administering to a patient in need thereof, an effective amount of a compound disclosed above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 illustrates the bimodal distribution of binding affinities.

DESCRIPTION OF BEST AND VARIOUS MODES

Compounds of the present disclosure are represented by the following formulae:

1 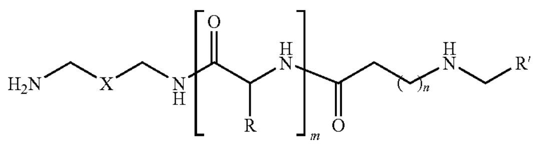 and

2 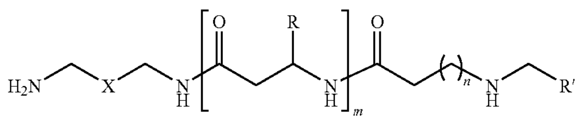 wherein x is selected from the group consisting of $—(CH_2)_y—$; 1,2-$C_6H_4—$; 1,3-$C_6H_4—$; 1,4-$C_6H_4—$; and $—CH_2\,OCH_2—$;

y is an integer of 0-10;

R is selected from the group consisting of —H, $—CH_3$, $—CH_2C_6H_5$, $—CH_2$-3-indoline, $—CH_2$-2-indoline, and $—CH_2$-4-imidazole m is 0-4;

n is 0-4; and

R' is selected from the group consisting of $—(CH_2)_o—CH_3$; $—(CH_2)_o—CH_2NH_2$; phenyl; 1-naphthyl and 2-naphthyl;

o is an integer of 0-16;

pharmaceutically acceptable salts thereof; and prodrugs thereof.

Preferred compounds according to the present disclosure are represented by the following formulae:

1. formula for MQTS 1172:

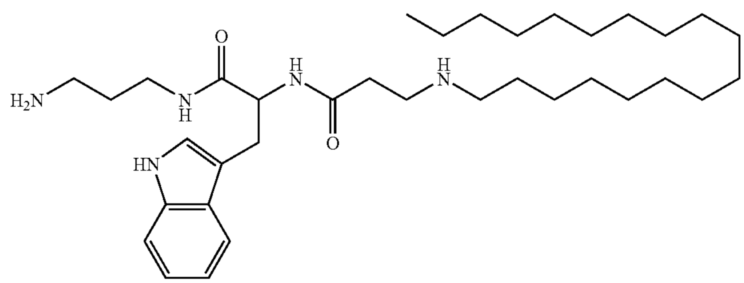

and, 2. formula for MQTS 1132:

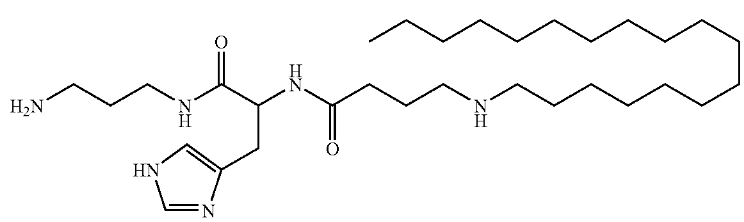

and,

3. The formula for MQTS 1007:

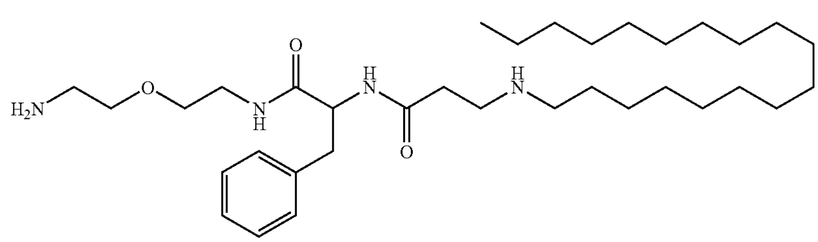

and,

Figure 1:
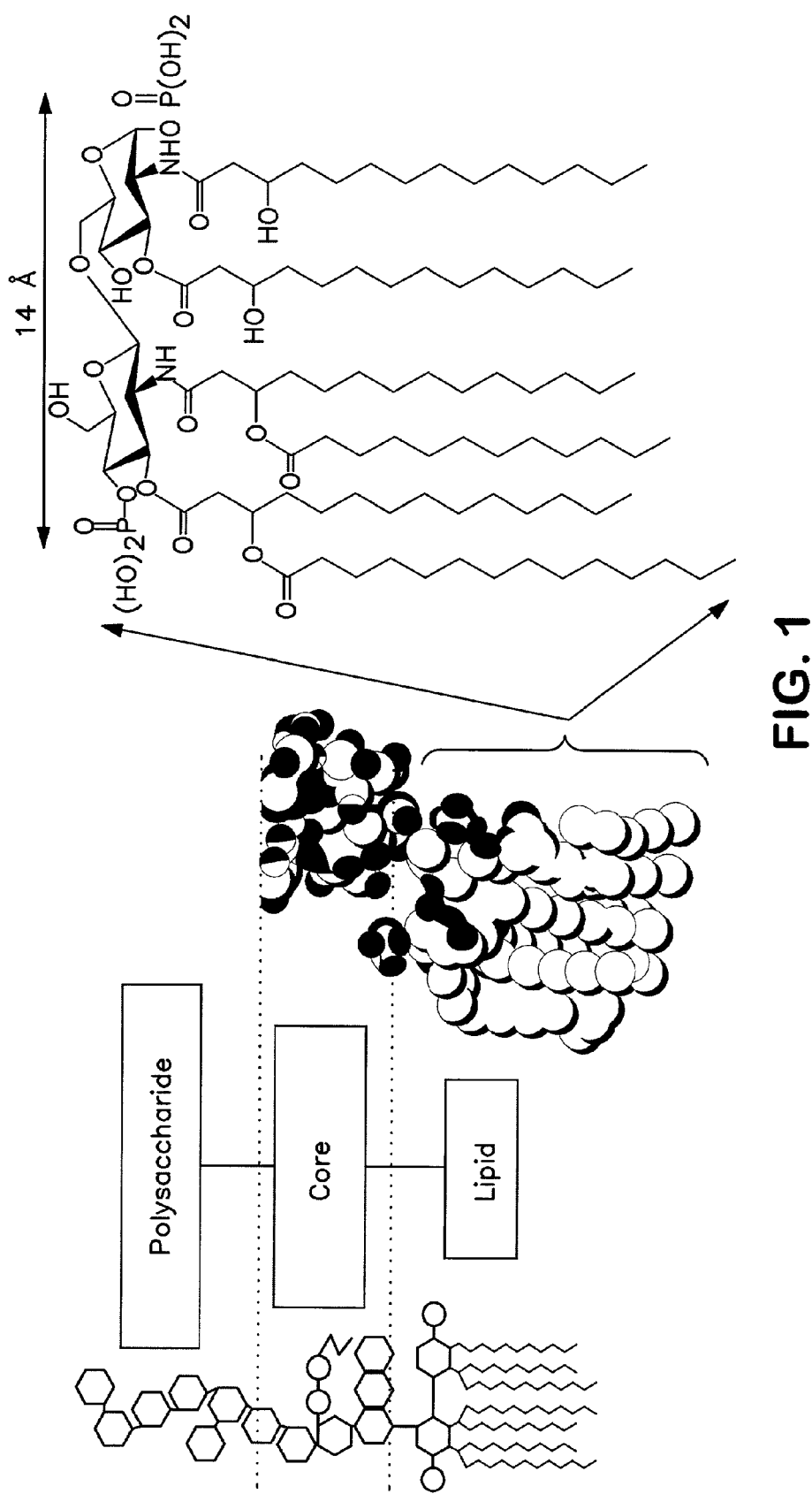
FIG. 1 shows a schematic and crystal structure of lipopolysaccharide along with Lipid A.

4. The formula for MQTS 1242:

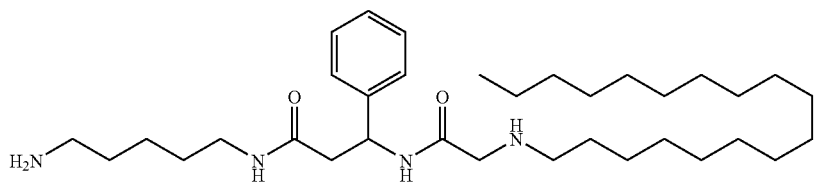

Further preferred compounds, representing 1,3-C$_6$H$_4$—molecular arrangement as specified above, according to the present disclosure are represented by the following formulae:

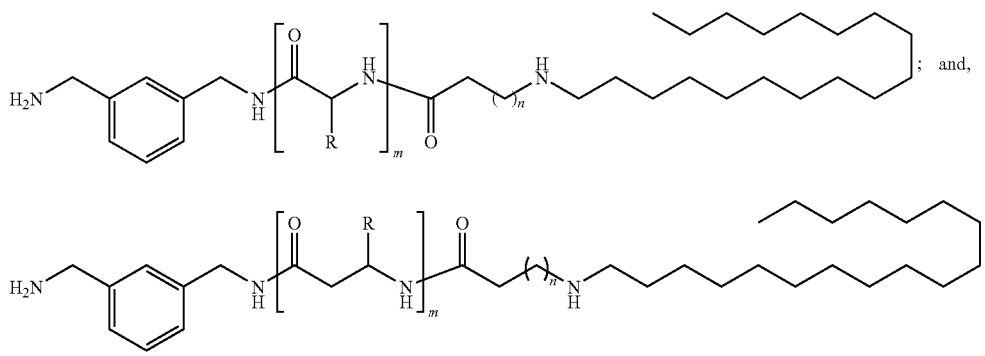

According to the present disclosure a terminally-placed long-chain aliphatic group is important for effective LPS neutralization. Furthermore, the chemical space defined by the described compounds identify novel, non-polyamine scaffolds that incorporate the LPS-binding pharmacophore described above.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R

Carbamates, —NHC(O)OR (Acyloxy)alkyl Carbamates, NHC(O)OROC(O)R

Enamines, —NHCR(=CHCRO$_2$R) or —NHCR(=CH-CRONR$_2$)

Schiff Bases, —N=CR$_2$

Mannich Bases (from carboximide compounds), RCONHCH$_2$NR$_2$

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels.

Another prodrug derived from a carboxylic acid form of the invention may be a quaternary salt type

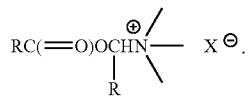

of structure described by Bodor et al., J. Med. Chem. 1980, 23, 469.

It is of course understood that the compounds of the present disclosure relate to all optical isomers and stereo-isomers at the various possible atoms of the molecule.

The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

The compounds may be utilized alone or in combination with other agents.

In another aspect of the disclosure, compositions containing the above described compounds and derivatives are provided. Typically, the compositions are formulated to be suitable for pharmaceutical use by the inclusion of appropriate carriers or excipients.

In a further aspect of the disclosure methods for the use of the above described compounds, as well as compositions, are provided. These methods include uses of the invention's compounds to modulate or interrupt biological processes involving the recognition or binding of oligosaccharides-based biomolecules. Compounds of the present disclosure are useful for treating a disease or condition in which the inhibition of NO (nitric oxide) is desirable. Examples of human diseases and conditions include, but are not limited to, chronic or acute inflammation, inflammatory bowel disease (including Crohn's disease), inflammatory bowel syndrome, autoimmune diseases rheumatoid arthritis, systemic lupus erythematosus, cutaneous forms of lupus, Type 1 and Type 2 diabetes, multiple sclerosis, psoriasis, spondyloarthropathies (SpA) including spondylitis, synovitis, psoriatic arthritis and subclinical gut inflammation and infectious diseases including sepsis, septic shock, endotoxic shock, HIV and other viral infections including cytomegalovirus, herpes simplex virus, influenza virus; infectious disorders caused by bacteria or fungi.

As discussed above, the present disclosure describes an example of a method to selectively interrupt oligosaccharide-mediated biological phenomenon. The method recognizes the exhaustive number of potential biological and drug targets involving oligosaccharide conjugates. The molecular contributions for binding to lipid A/endotoxin, one of a number of these anionic oligosaccharide targets, were assessed in a rapid and detailed fashion through the application of a prospectively designed, moderately-sized 540-membered example library. Analysis of the contribution that each individual monomeric library component made to the most tight-binding analogs was facilitated by use of "molecular vector analysis." This analysis confirmed the importance of the lipophilic long chain aliphatic group (typically $C_{12}$ to $C_{22}$ lipid chain and more typically $C_{18}$ lipid chain), while also pointing to the contribution made by heteroaromatic moieties such as indole portion of tryptophan. The incorporation of techniques such as Synphase lanterns together with the data transfer/handling software made synthesis of the multi-hundred membered library much more straightforward.

The following non-limiting examples are presented to further illustrate the present disclosure.

General experimental methods. The sources of all chemical reagents and starting materials are of the highest grade available and are used without further purification. Lanterns used are MIMOTOPES SYNPHASE PS D-SERIES LANTERNS™ with a trityl alcohol linker. Thin-layer chromatography analysis and column chromatography is performed using Merck $F_{254}$ silica gel plates and Baker 40 μm flash chromatography packing, respectively. TLC analysis used the specified solvent systems with detection by ninhydrin staining. Data handling is facilitated by the use of BalanceLink V3.0 software from Mettler-Toledo to enable transfer of weight values directly into an Excel spreadsheet. Solvents from resin cleavage are removed through the use of a Savant centrifugal evaporator operating at 25° C.

LC/MS analyzes are performed using a Gilson 322 HPLC system coupled to a 215 liquid handler. Detection was by a Finnigan AQA operating in ESI$^+$ mode (m/z range 140 to 1600 amu) together with an Agilent 1100 series diode array detector (UV range 220 to 320 nm). Gradient elution from 2 to 7 min. at 0.2 mL/min. is performed using 2% to 100% $CH_3CN$ in $H_2O$ (both with 0.05% TFA) using a Waters XTerra MS $C_{18}$ 2.1×150 mm (3.5 μm) column. $^1$H NMR spectra are recorded at 300 MHz on a Bruker AV300 spectrometer at the University of Washington, Seattle. $^1$H NMR signals are generally multiples unless otherwise noted as s=singlet, d=doublet, t=triplet or m=multiplet. Chemical shifts are relative to external 3-(trimethylsilyl)-1-propanesulfonic acid, sodium salt.

EXAMPLE 1

Ethyl N-(2-nitrophenylsulfonamide)-glycinate (2a)—To a solution of 25.11 g (0.180 mole) of ethyl glycinate hydrochloride and 42.11 g (0.190 mole, 1.06 eq) of 2-nitrophenylsulfonylchloride in 400 mL of dry $CH_2Cl_2$ at 0° C. is added 76.6 mL (0.44 mole, 2.44 eq) of $^i$Pr$_2$NEt dropwise. The resulting solution is stirred for 18 h when it is quenched by the addition of 200 mL of $H_2O$. The organic layer is removed and the aqueous part is re-extracted by an additional portion of 200 mL $CH_2Cl_2$. The combined organic layers are washed with 0.1 N HCl then brine and dried and evaporated to give the crude product as an off-white solid. This is crystallized from 400 mL of abs. EtOH to give 44.69 g (90%) white crystals. $^1$H NMR (CDCl$_3$, δ): 8.16 (d, 1H), 7.82 (d, 1H), 7.78 (m, 2H), 5.62 (s, 1H), 4.04 (q, 2H), 3.98 (s, 2H), 1.24 (t, 3H).

EXAMPLE 2

Ethyl N-(2-nitrophenylsulfonamide)-2-aminopropionate (2b)—Using the procedure described above this product is produced in 80% yield. $^1$H NMR (CDCl$_3$, δ): 8.24 (d, 1H), 7.81 (d, 1H), 7.74 (m, 2H), 5.75 (s, 1H), 4.11 (q, 2H), 3.43 (q, 2H), 3.23 (m, 2H), 2.43 (t, 2H), 1.22 (t, 3H).

EXAMPLE 3

Ethyl N-(2-nitrophenylsulfonamide)-3-aminobutyrate (2c)—Using the procedure described for 2a, this product is produced in 54% yield following crystallization from abs. EtOH. $^1$H NMR (CDCl$_3$, δ): 8.21 (d, 1H), 7.84 (d, 1H), 7.77 (m, 2H), 5.65 (s, 1H), 4.09 (q, 2H), 3.42 (q, 2H), 3.23 (m, 2H), 2.43 (t, 2H), 1.91 (m, 2H), 1.25 (t, 3H).

EXAMPLE 4

General alkylated monomer synthesis—Mitsunobu alkylation: Ethyl N-2-(1-naphthyl)ethyl-(2-nitrophenylsulfonamide)-2-aminopropionate (3b1)—To the solution produced by dissolving 3.02 g (10 mmol) of 2b, 1.72 g (10 mmol) of 2-(1-naphthyl)-ethanol and 3.98 g (15 mmol) of triphenylphosphine in 50 mL of dry $CH_2Cl_2$ is added dropwise at 25° C. a solution of 2.95 mL (15 mmol) of diisopropylazodicarboxylate in 15 mL of dry $CH_2Cl_2$. The resulting yellow colored solution is stirred for 16 h when the reaction solution is diluted in 75 mL $CH_2Cl_2$ and 75 mL 0.1N HCl. The aqueous layer is removed and re-extracted by an additional 75 mL portion of $CH_2Cl_2$. The combined organic layers are washed with brine, dried and evaporated to give the crude product as a yellow oil. Column chromatography over silica gel uses 3:1 hexane/ethyl acetate to give 2.17 g (48% yield) colorless crystals.

EXAMPLE 5

Ester hydrolysis: N-2-(1-naphthyl)ethyl-(2-nitrophenylsulfonamide)-2-aminopropionic acid (4b1)—To the clear solution of 3.17 g (6.9 mmol) of 3b1 in 100 mL of THF is added 13.9 mL (2 eq) of 2N LiOH in $H_2O$. The resulting two-phase mixture is vigorously stirred for 16 h when the THF is evaporated in vacuo and the resulting residue is suspended in 75 mL $CH_2Cl_2$ and 50 mL of 1N HCl. The aqueous part is re-extracted by an additional portion of 75 mL $CH_2Cl_2$ and the combined organic layers are dried and evaporated to give oily solids. When TLC analysis using 1:1 hex/EtOAc with $I_2$-detection shows the presence of diisopropylhydrazine side-product column chromatography with 8:2 hex/EtOAc can be used to obtain pure carboxylic acid monomer material.

15-Membered test library production. A set of 15 MIMOTOPES SYNPHASE PS D-SERIES LANTERNS™ with a trityl alcohol linker (15×35 µmol=0.525 mmol total) are labeled with spindles and cogs and dried under high vacuum over $P_2O_5$ for 18 h. They are then suspended in a solution of 18 mL dry $CH_2Cl_2$ and 2 mL of acetyl chloride. Following gentle shaking for 3.5 h the lanterns are washed three times with dry $CH_2Cl_2$ to give P1. While still in their $CH_2Cl_2$ swollen form they are suspended in 20 mL of dry $CH_2Cl_2$ and 5 mL of 3-aminopropanol is added. The vessel is shaken for 18 h then washed three times each with $CH_2Cl_2$, DMF, $^i$PrOH, THF and $CH_2Cl_2$ (standard washing sequence) then is dried under high vacuum giving P2.

The lanterns are next transformed into their amine form (P4) by the following two-step sequence. Suspension in 20 mL dry $CH_2Cl_2$ is followed by the addition of 0.39 g (2.63 mmol, 5 eq) of phthalimide and 0.69 g (5 eq) of triphenylphosphine as solids. The reaction vessel is shaken to dissolve these reagents then treated portionwise with a solution of 0.52 mL of diisopropyldiazodicarboxylate dissolved in 10 mL of dry $CH_2Cl_2$. This vessel is shaken for 3 h when standard washing and drying give lanterns P3. These are suspended in 10 mL of abs. EtOH and treated with 10 mL of hydrazine hydrate. The vessel is tightly capped then heated to 60° C. in a rotating oven for 18 h. Following cooling to room temperature the lanterns are washed and dried in standard manner to give lantern form P4.

Fmoc-amino acid couplings use the following standard conditions for production of lanterns P5. The amino lanterns P4 are suspended and swelled in 5 mL of dry DMF. A solution containing 1.02 g (2.63 mmol, 5 eq) of Fmoc-Phe-OH, 1.0 g (5 eq) of HBTU, 0.2 g (2.5 eq) of HOBt and 0.92 mL (10 eq) of $^i$Pr$_2$NEt is prepared and shaken for 10 min prior to addition to the lanterns suspended above. The resulting reaction mixture is shaken gently for 2 h when standard washing and drying give the product lanterns P5. The peptide coupling and resin loading of the lanterns is measured by dilution of the solution from next, Fmoc-group removal reaction. The lanterns are suspended in 15 mL 20% piperidine in DMF and shaken for 15 min. A 0.10 mL aliquot is removed and diluted to 10 mL in the same solvent mixture. Following solvent zeroing a UV measurement of the absorbance at 301 nm gives a value of 1.186. Using the $\epsilon_a$ value for Fmoc-piperidine adduct of 14102 L mol$^{-1}$ cm$^{-1}$ a loading efficiency of 16.7 µmole or 48% is calculated (1.186×14102=16.7) (Manufacturer's stated loading was 35 µmole). Standard washing and drying of the lanterns following a 1.5 h reaction time gives lanterns P6.

These lanterns are now used to couple, individually, to each of the 15 monomers synthesized through the process described above. Fifteen 4 mL dried vials are loaded with 0.066 g (0.14 mmol, 4 eq based on an avg MW of 474.4) of each monomer. One mL of a solution that is prepared containing 0.80 g (2.1 mmol, 4×15 eq) of HBTU, 0.16 g (1.05 mmol, 2×15 eq) of HOBt and 0.732 mL (4.2 mmol, 8 eq) of $^i$Pr$_2$NEt in 15 mL of dry DMF is added to each monomer containing vial. These vials are gently shaken while the lanterns are pre-swelled together in 15 mL of dry DMF. After 10 min each labeled lantern is placed into its respective vial containing the activated monomer ester. The lanterns are shaken overnight then the reaction solution is decanted. They are combined and washed in standard fashion. Drying gaies the protected lanterns P7. The NPS group is removed by treating the combined set of lanterns with 5 mL of 2-mercaptoethanol, 5 mL of DBU and 15 mL of DMF for 18 h. Standard washing and drying gives the loaded resins P8 ready for cleavage.

Each lantern is placed in an individually marked and pretared 4 mL vial and treated with 2.0 mL of cleavage cocktail consisting of 80:18:2 $CH_2Cl_2$/TFA/$^i$Pr$_3$SiH for 1 h. The lanterns are extracted with tweezers and washed with $CH_2Cl_2$ and the cleavage solutions are evaporated. The resulting yellow oil residues are each dissolved in 0.50 mL MeOH and 20 µL removed and diluted to 200 µL in $H_2O$ for LC/MS analysis. LC/MS is performed on all fifteen analogs. The concentrated stock MeOH solutions are also used for TLC analysis in two solvent systems: a) 8:2 $CH_3CN$/concd $NH_4OH$; b) 90:8:2 $CHCl_3$/MeOH/concd $NH_4OH$. $^1$H NMR is performed on two analogs below.

MQTS 1093T—LC/MS calcd [M+H] for $C_{27}H_{32}N_4O_2$: m/z 445; obsd 445 at 13.6 min. $^1$H NMR ($D_2O$, δ): 7.73-7.16 (m, 14H), 4.38 (t, 1H), 4.22 (m, 2H), 3.84 (m, 2H), 3.32-2.83 (m, 2H), 2.60 (m, 2H), 2.02 (m, 2H), 1.60 (m, 2H).

MQTS 1095T—LC/MS calcd [M+H] for $C_{17}H_{29}N_5O_2$: m/z 336; obsd 336 at 12.9 min. $^1$H NMR ($D_2O$, δ): 7.38-7.20 (m, 5H), 4.51 (t, 1H), 3.86 (m, 2H), 3.30-3.15 (m, 2H), 3.06 (t, 8H), 2.02 (m, 2H), 1.62 (m, 2H).

540-Membered example library production. Synthesis of the complete 540-membered library follows the same sequence as that for the 15-membered test library. 540 lanterns are labeled with spindles and cogs and are activated to their P1 forms using the procedure above. Six sets of 90 lanterns are sorted into individual vessels and are treated with 10 g (or 10 mL) of the amino alcohol shown in Chart 1. Following reaction and washing to give their P2 forms the 540 lanterns are re-combined and converted to their free amine form via the sequence outlined above (P2 to P4). The lanterns are then split into six groups with 90 members and coupled to the requisite Fmoc-amino acid using the procedure outlined above. UV analysis of the Fmoc-loading of six randomly selected lanterns showed respectable 60-125% loading efficiencies. Following couplings the re-combined lanterns are treated with 20% piperidine/DMF as above to give the free-amine form P6 lanterns. The lanterns are then split (36×15)

for their final coupling reaction to the 15 monomers 4 using the standard coupling conditions. NPS-protecting group cleavage readies the lanterns for sorting into 540 individual pre-tared 4 mL vials. Final cleavage gives the crude analogs MQTS 1001 to 1540 in their TFA salt forms. An average yield of 84% is calculated based on the expected structure and excluding those with >200% yield (n=36).

The entire library is characterized by TLC and LC/MS. The crude material is mostly dissolved in 1.0 mL of MeOH and spotted onto TLC plates. If insoluble particles remain they are removed by filtration prior to chemical or biological characterization. Elution of the plates use the solvent system $CHCl_3$/MeOH/concd $NH_4OH$ 85:13:2 with ninhydrin detection. The above concentrated stock solutions are diluted 20× into 1% TFA in $H_2O$ for LC/MS analysis. The MeOH sample solutions are treated with 1.0 mL of 6N HCl then evaporated to give the HCl salts of the final products. These are dissolved in the amount of 20% DMSO/$H_2O$ that is required to give 20 mM solutions based on the crude yields that are obtained. The use of an Excel spreadsheet with the pre-tared and final vial weights together with MQTS number, structures, molecular formula, and molecular weights of free bases imported from ISIS base greatly facilitate the calculations of salt molecular weights, percent yields and amount of solvent necessary to give bioscreening solutions.

Rationale and design of molecular scaffold and library monomers. The design of the example 540-membered library is to: i) to confirm and validate the lipid A binding pharmacophore in compounds with non-polyamine scaffolds; ii) to maximize diversity of library members within this context; iii) to systematically test the hypotheses that the introduction of aromatic groups and/or H-bond donor/acceptor atoms in the scaffold enhance binding affinity. Several potential strategies to enhance carbohydrate-binding affinity are used by targeting additional interactions with the diglucosamine backbone of lipid A. Both covalent (such as by using boronates which form esters with the vicinal cis diols)[62;63] as well as noncovalent interactions[64;65] are considered. An examination of the Protein Data Bank for lectin-sugar complexes[66;67] as well as relevant literature[68-70] point to (a) multiple H-bond donor/acceptor pairs contributing to the enthalpy of binding and (b) an unusual preponderance of aromatic side chains around the sugar binding site,[66] suggesting either multiple CH-π[71;72] or OH-π weak H-bonds.[73;74] Indeed, a lipid A receptor with a oligocyclopentane backbone substituted with amino and indole functionalities has been described.[75] A recent report described LPS-targeting peptoids isolated from a positional scanning library which incorporated various aromatic constituents along its backbone.[76] Furthermore, the crystal structure of LPS indicates a range of inter-atomic distances between 2.4-4 Å between H-bond donor/acceptor atoms on the lipid A backbone (see FIG. 1).[77] Library members are therefore designed with an intervening distance of 2-3 carbon bonds between H-bond donor/acceptor atoms in order to favor complementarity with the anionic carbohydrate target.

The scaffold and elements (PORTIONS 1-3) of the combinatorial library are shown in Chart 1. The distance between the terminal amines are 'dialed in' by varying intervening elements in both PORTION 1 as well as the Gly/Ala/GABA amino acids in PORTION 3. As can be seen in Chart 1, PORTION 2 contains a preponderance of aromatic groups. In PORTION 3.y, both aliphatic and aromatic substituents are incorporated in order to meet the requirement of a long-chain aliphatic group for optimal activity.[61]

Synthesis of library monomers. Using a Mitsunobu-mediated alkylation of solid-phase 2-nitrophenylsulfonamides[78;] 79 is initially considered, but during the formation of the requisite resin-bound sulfonamides to completion is not achieved. Similar difficulties using this approach on solid-phase have been previously reported in the literature.[80] A solution-phase alkylation of the esters of amino-acid sulfonamides for the synthesis of the fifteen PORTION 3 monomers en route to the synthesis of the 540-membered library by the route depicted in Scheme 1 is instead employed. Modification of the conditions by the use of the more hindered base $^iPr_2NEt$ enables the desired sulfonamides to be prepared in good yield following crystallization.

Alkylation of each of the three sulfonamides by the five primary alcohols corresponding to the PORTION 3 substituents shown in Chart 1 proceeds in straightforward fashion. Following column chromatography purification some of these alkylated ester-sulfonamides show the presence of various amounts of an impurity corresponding to diisopropylhydrazinedicarboxylate, a side-product from the Mitsunobu alkylation. This material can be eliminated either at this ester material step (3a-c) or in the next, carboxylic acid step (4a-c) by column chromatography. In either case, the impurity is readily detected by TLC using $I^2$ staining or by $^1H$ NMR, ensuring its complete removal in the products. Hydrolysis of the esters is accomplished in a straightforward manner. All molecules show high purity by TLC and $^1H$ NMR with their identities being confirmed by LC/MS analysis.

Chemical route to library: Fifteen-membered test library. A test of the solid-phase synthetic route is carried out using each of the fifteen monomers produced above attached to fifteen identical lanterns containing the 1,3-diaminopropane-Phe PORTION 1: PORTION 2 resin partner (Scheme 2). Prior experience with symmetrical diamine attachment to tritylchloride solid-phase resin shows that significant crosslinking occurs leading to substantial diamine contamination in the cleaved products. For this reason a three-step sequence is used involving attachment of an amino alcohol followed by —OH to —$NH_2$ conversion. Mitsunobu-mediated phthalimide group attachment followed by hydrazine liberation of the free amine gives the desired lanterns. This process completely eliminates the formation of the diamine side-product while substantially increasing the loading efficiency of the desired product.

Standard peptide coupling conditions are used to add the Phe residue to this set of lanterns. UV analysis of the liberated Fmoc group from the next step shows a loading efficiency of 48% at this stage. The lanterns are then individually attached to each of the fifteen monomers using HBTU coupling conditions. The NPS-groups are removed using 2-mercaptoethanol/DBU/DMF. The products are then cleaved using 80:18:2 $CH_2Cl_2$/TFA/$^iPr_3SiH$ directly into individual pre-tared 4 mL vials. Data handling is facilitated by direct data acquisition from the weighing balance into a spreadsheet program. In this way, data associated with the samples including vial tare weight and net crude weight can be coordinated with the sample ID number, structure, molecular weight, theoretical yield, and crude percent yield. The samples are dissolved in MeOH and sampled for TLC and LC/MS analyses as described below. These crude samples are then treated with an equal volume of 6N HCl and evaporated to give their per-HCl salts. For the fifteen test samples an average weight percent yield of 70% is calculated represented by an average crude weight of 18.4 mg.

TLC and LC/MS analysis of the crude samples support the viability of the 8-step process. Several informative observations are made following this analysis: 1) Side-products with masses at 147 amu lower m/z values are observed. Two major spots are seen in the TLC analysis of most of these test analogs and a side-peak showed up at a shorter retention times in the LC/MS chromatograms. It is deduced that these side-products are generated from the incomplete coupling of the Phe-PORTION 2 residue. It is concluded that this lower than desired Phe loading gives rise to substantial amounts of truncated products in the samples and may explain the lower than expected 48% loading efficiency measured following this step. 2) Alkene addition products are observed with the unsaturated PORTION 3.x4 monomers. A mixture of un- and mono-substituted TFA-adducts are seen. Subsequent analysis of the HCl salts showed complete exchange of $^-$OTFA by $^-$Cl. By carrying out a test library synthesis it is reasoned that PORTION 2 loading conditions should be modified to decrease truncated side-product formation. Furthermore, it is determined that the cleavage conditions do not completely eliminate side-product formation involving acid-mediated alkene addition.

Synthesis of 540-membered example library. A coding system is devised to label the lanterns and the entire library's structures are enumerated into an ISIS™ database. A spreadsheet is configured for handling the data generated. Library production follows the route outlined in Scheme 2 and utilizes the components shown in Chart 1. A large excess of the six amino alcohols is used to elaborate 90 labeled lanterns in six individual vessels. The lanterns are then recombined for the next two-step —OH to —NH$_2$ conversion. Splitting and sorting enable the next PORTION 2 components to be added. The number of equivalents of Fmoc-amino acid used in this step is increased from 4 to 5 in order to decrease the amount of incomplete addition products. The loading is improved by UV analysis of the liberated Fmoc-piperidine adduct from a selection of individual lanterns with different PORTION 1: PORTION 2 components. An average loading of 109% (relative to the manufacturer's value of 35 µmole) is obtained.

The Fmoc-groups are removed from the entire library and the monomer set is coupled to fifteen sets of 36 lanterns each. The NPS-grouping is removed and the lanterns are sorted into individual pre-tared vials in preparation for final cleavage. Cleavage occurs in similar fashion to that described above and gives an average of 84% yield of the hydrochloride salt of the crude products. TLC and LC/MS analysis of the entire set of compounds show adequate purity for the majority of the library and confirmed that each contain the desired product as the major component. Side-products due to truncated PORTION 2 addition are absent but acid-mediated addition products to some alkene containing products is still observed. The crude library is dissolved in 20% DMSO/H$_2$O at 20 mM and is screened in the assays described below.

Quantitative Estimation of LPS Binding Affinity. The relative binding affinities of the entire library of analogs with a recently-described high-throughput fluorescence based displacement assay, is examined using BODIPY-TR cadaverine (BC).[81;82] Results are reported as half-maximal effective displacement of probe (ED$_{50}$). In all experiments, Polymyxin B (PMB), a decapeptide antibiotic, known to bind and neutralize LPS,[83-86] is used as a reference compound.

Figure 3:
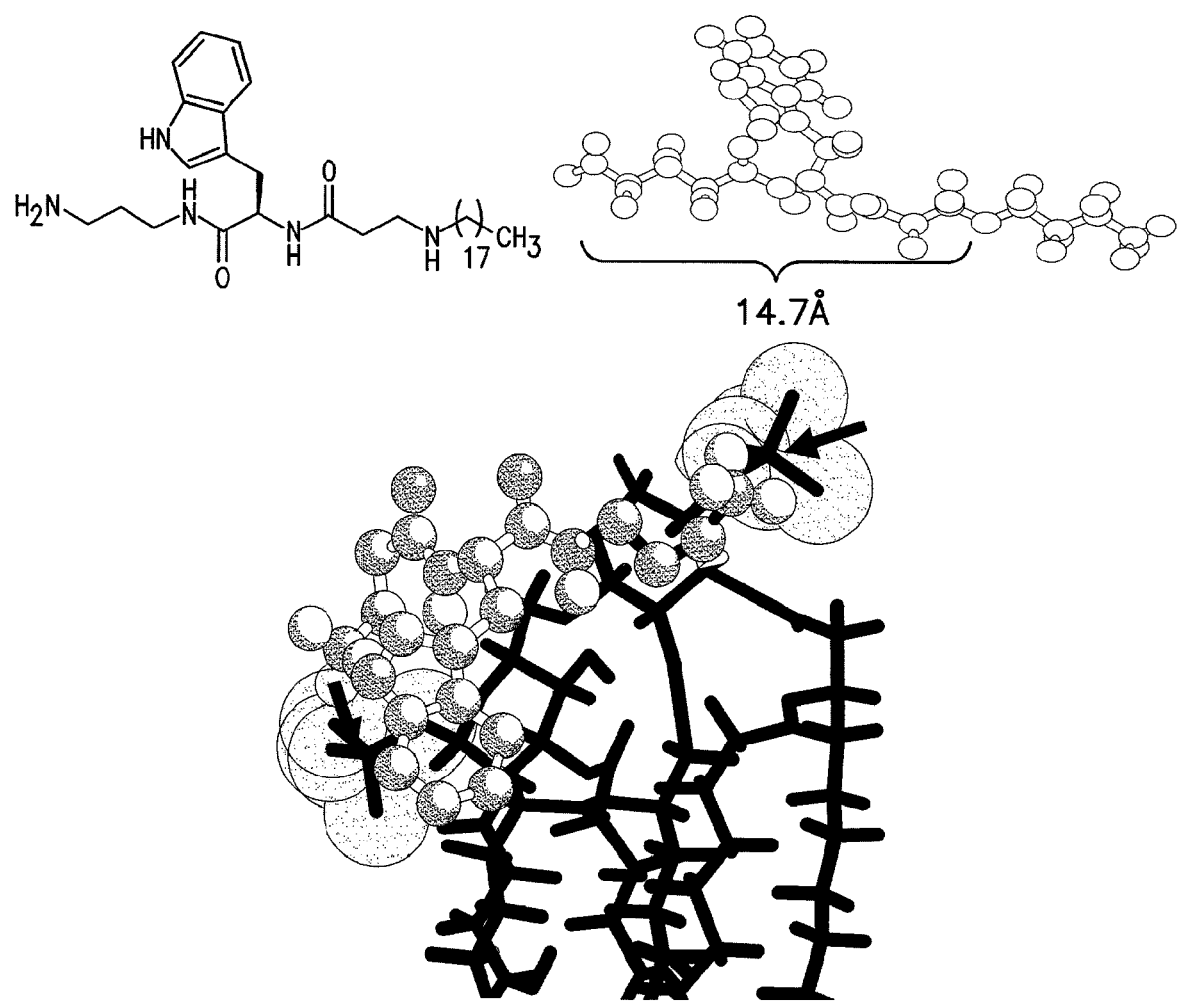
FIG. 3 illustrates an energy-minimized model of the disclosed scaffold-lipid A complex.

As shown in FIG. 2, a distinct biphasic distribution of binding affinities can be observed, with a clear demarcation of high- and low-affinity compounds. A particularly instructive method of graphical evaluation of library screening results is shown in FIG. 3. This methodology is referred to herein as 'molecular vector analysis'; and it involves counting the number of occurrences of each individual monomer in the subset of analogs in the top binders (52 analogs with ED$_{50}$<10 µM), and the frequency of monomers in weak-binding compounds (488 analogs with ED$_{50}$>10 µM). The resulting histograms are easy to interpret, and simple statistical analyses ($\chi$-square) can be employed to verify the importance of those building blocks that contribute most to the resulting binding.

The most profound effects on activity appear with the selection of long chain hydrophobic C$_{18}$ chain (PORTION 3.x.2) and by the selection of an indole moiety (Trp) in the PORTION 2 position. More subtle, albeit no less important, insights can be gleaned from the observations made concerning selection of PORTION 1 and PORTION 3 monomers. It would appear that the original concept of "distance dialing"[61;82;87;88] designed into the library play a role in the results observed. The incorporation of PORTION 1 monomer 1,3-diaminopropane gives an unexpectedly high population of members in the top 52 samples. Likewise, selection of 2-aminopropionic acid for PORTION 3.B lead to a higher number of tight binders than the other two monomer components. Based on prior work,[61;82;88-90] this is attributed to a better congruence in the distance between the two terminal protonatable nitrogen atoms in this subset of analogs and that between the anionic phosphates on the lipid A backbone, enabling effective ionic H-bonds between the charged groups. It is therefore instructive to construct the "best" scaffold using the optimal PORTION 1 "vector" component 1,3-diaminopropane, Trp in PORTION 2, and a PORTION 3 bearing a C$_{18}$ alkyl group. The backbone of this molecule (without the C$_{18}$ alkyl chain) is then docked on a crystal structure-derived[77;91] model of lipid A using AutoDock[92;93]. The alkyl chain is omitted in the modeling since it has previously been observed that the force fields within AutoDock do not adequately reflect hydrophobic interactions for glycolipids, such as lipid A. In the energy-minimized model of the docked scaffold-lipid A complex, (FIG. 3), a distance of 14.7 Å is observed between the terminal amines, matching very closely the previously determined optimized distance between protonatable amine groups in LPS binders.[55;82;88;90] The O atoms on the lipid A phosphates are also found to be within H-bonding distances of the amines (FIG. 3). Other PORTION 1 monomer components such as those composed of 1,5-diaminopentane, significantly diverge from the optimal value and consequently do not bind LPS as well (FIG. 2).

Re-synthesis of active molecules. Based on the combination of results from the binding and preliminary NO inhibition assays, a series of 25 analogs is selected for re-synthesis and purification (Table 1). In order to provide enough material for purification, we used two lanterns are used for each individual analog. As previously seen in the fifteen test-analog series, minor amounts of truncated (-PORTION 2 amino-acid) species are seen with several of these examples. It is possible to isolate 9 molecules representing these truncated analogs (Table 1). The same synthetic route is used as before and the crude products are purified over 900 mg disposal SiO$_2$ solid-phase extraction columns. These purified analogs show greater than 90% purity when analyzed by TLC and LC/MS methods. Table 1 shows the MQTS numbers, structures and BC-binding data (ED$_{50}$ values) together with NO inhibition data (IC$_{50}$ values).

Figure 4:
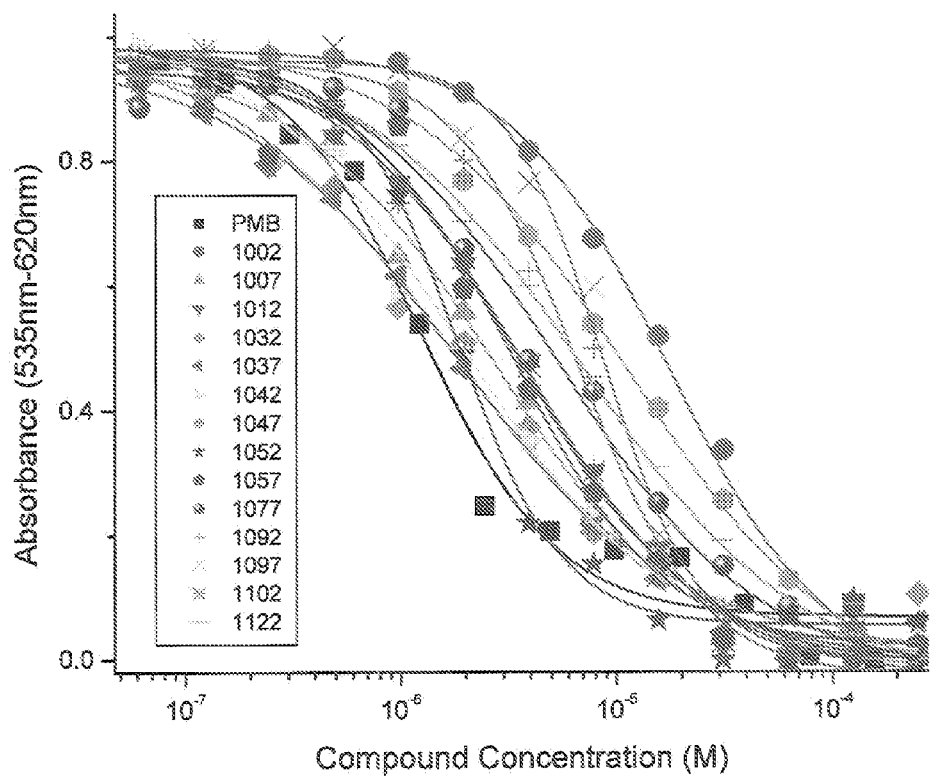
FIG. 4 illustrates ability of compounds of the disclosure to inhibit NO production.
Figure 5:
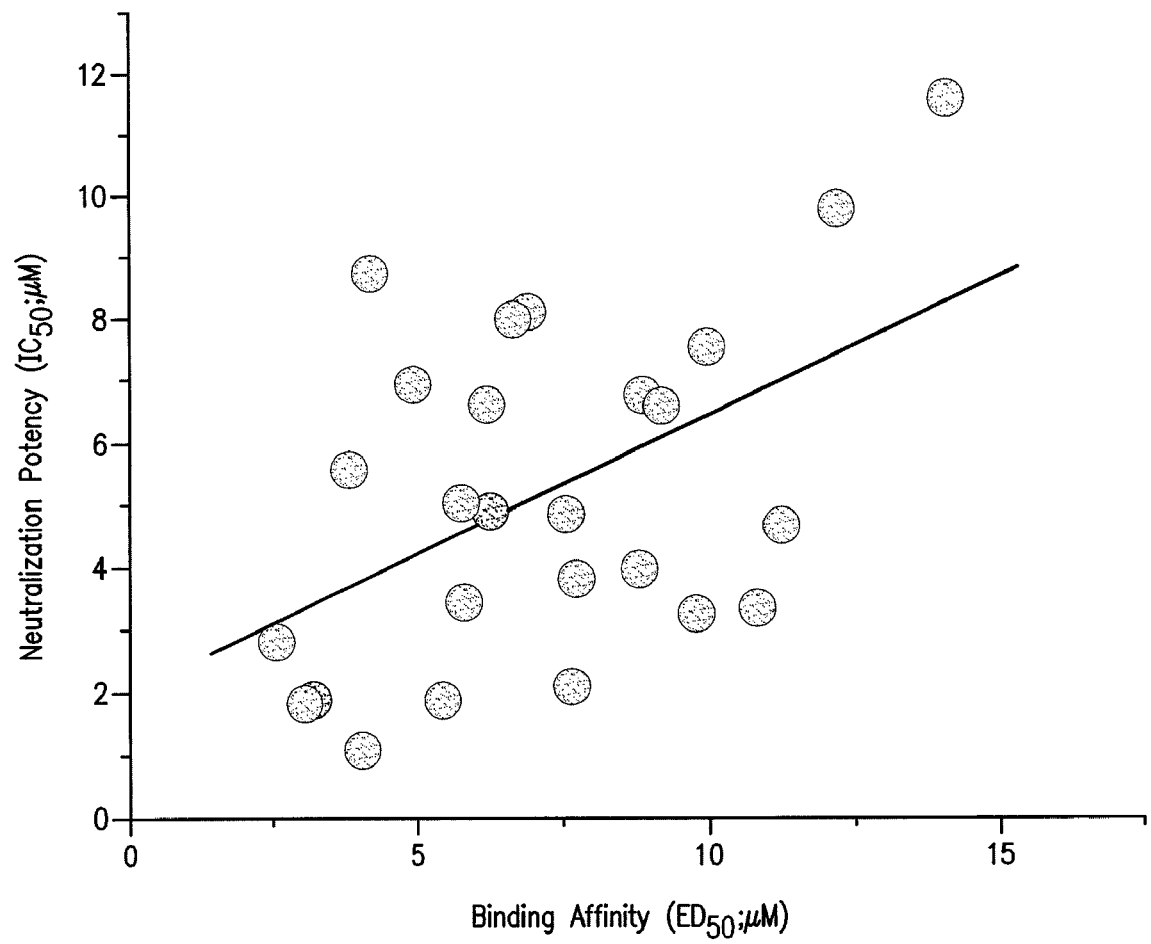
FIG. 5 illustrates the correlation of binding affirmative to neutralization patterning.

Assessment of neutralization of LPS toxicity: NO inhibition activity. Murine monocytes (J774.A1 cells) produce measurable quantities of NO upon exposure to LPS and provide a high-throughput and validated model for the rapid and quantitative assessment of compounds in neutralizing the toxicity of LPS.[81;82;94] Compounds that neutralize LPS inhibit NO production in a dose-dependent manner from which 50% inhibitory concentrations (IC$_{50}$) were determined (FIG. 4). The analogs determined to have the highest affinity in the BC-binding assay are then assayed in this NO inhibition assay (Table 1). Results in this assay parallel those in the binding assay (FIG. 5).

Hit re-synthesis and characterization. Two lanterns per analog are used to resynthesize the analogs shown in Table 1. Synthesis follow the procedures given above. The resulting crude products in their TFA salt forms are purified over disposable Alltech SPE cartridges containing 900 mg of $SiO_2$. Chromatography uses 5 to 20% MeOH in $CH_2Cl_2$ with 1% concd $NH_4OH$. TLC solvent is 80:18:2 $CH_2Cl_2$/MeOH/concd $NH_4OH$ with detection by ninhydrin. The product containing fractions are pooled and evaporated then converted to their per-HCl salt forms by treatment with 6N HCl in MeOH and re-evaporation. In several cases shown in Table 1, truncated analogs (MQTS 2322-2330) without the internal amino acid portion are also isolated from these products. Purified samples are analyzed by $^1$H NMR, TLC and LC/MS using the methods described above. A selection of LC/MS and NMR data is given here. Yields for these products range from 6 to 25% following the 8-step solid-phase route and all show over 90% purity by the methods noted.

MQTS 1002—2.9 mg (6% yield) white solid is obtained. LC/MS calcd [M+H] for $C_{33}H_{60}N_4O_3$: m/z 562; obsd 562 at 14.2 min. $^1$H NMR ($D_2O$, δ): 7.35-6.92 (m, 5H), 3.86 (m, 1H), 3.68 (m, 2H), 3.57 (m, 2H), 3.39 (m, 4H), 3.14 (m, 4H), 2.98 (m, 2H), 1.63 (m, 2H), 1.17 (s, 30H), 0.80 (s, 3H).

MQTS 1007—5.3 mg (12% yield) white solid is obtained. LC/MS calcd [M+H] for $C_{34}H_{62}N_4O_3$: m/z 575; obsd 575 at 14.7 min. $^1$H NMR ($D_2O$, δ): 7.38-6.97 (m, 5H), 4.56 (m, 1H), 3.63 (t, 2H), 3.48 (m, 2H), 3.31 (m, 2H), 3.14 (m, 4H), 2.83 (m, 2H), 2.60 (m, 4H), 1.42 (m, 2H), 1.18 (s, 30H), 0.82 (t, 3H)

MQTS 1012—3.6 mg (8% yield) white solid is obtained. LC/MS calcd [M+H] for $C_{35}H_{64}N_4O_3$: m/z 590; obsd 590 at 14.7 min. $^1$H NMR ($D_2O$, δ): 7.36-6.94 (m, 5H), 4.58 (m, 1H), 3.63 (m, 2H), 3.52 (m, 2H), 3.32 (m, 2H), 3.11 (m, 4H), 2.55 (m, 2H), 2.28 (m, 2H), 1.63 (m, 2H), 1.50 (m, 2H), 1.17 (s, 32H), 0.80 (t, 3H).

MQTS 1032—6.3 mg (14% yield) white solid is obtained. LC/MS calcd [M+H] for $C_{30}H_{58}N_6O_3$: m/z 552; obsd 552 at 13.0 min. $^1$H NMR ($D_2O$, δ): 8.53 (s, 1H), 7.28 (s, 1H), 3.93 (s, 1H), 3.63 (t, 2H), 3.48 (m, 2H), 3.32 (m, 2H), 3.11 (m, 4H), 3.01 (m, 2H), 1.66 (m, 2H), 1.20 (s, 32H), 0.79 (t, 3H).

MQTS 1037—5.7 mg (13% yield) white solid is obtained. LC/MS calcd [M+H] for $C_{31}H_{60}N_6O_3$: m/z 566; obsd 566 at 12.9 min. $^1$H NMR ($D_2O$, δ): 8.58 (s, 1H), 7.26 (s, 1H), 4.58 (t, 1H), 3.63 (s, 2H), 3.47 (t, 2H), 3.28 (m, 2H), 3.31 (m, 2H), 3.12 (m, 4H), 2.98 (m, 2H), 2.78 (m, 2H), 1.65 (m, 2H), 1.20 (s, 30H), 0.78 (t, 3H).

MQTS 1042—8.1 mg (18% yield) white solid is obtained. LC/MS calcd [M+H] for $C_{32}H_{62}N_6O_3$: m/z 580; obsd 580 at 12.9 min. $^1$H NMR ($D_2O$, δ): 8.61 (s, 1H), 7.27 (s, 1H), 4.58 (t, 1H), 3.63 (t, 2H), 3.49 (m, 2H), 3.32 (m, 2H), 3.13 (m, 4H), 2.95 (m, 4H), 2.38 (m, 2H), 1.60 (m, 2H), 1.64 (m, 2H), 1.22 (s, 30H), 0.78 (t, 3H).

MQTS 1137—6.8 mg (19% yield) white solid is obtained. LC/MS calcd [M+H] for $C_{25}H_{52}N_4O_2$: m/z 441; obsd 441 at 13.3 min. $^1$H NMR ($D_2O$, δ): 3.96 (m, 2H), 3.28 (m, 4H), 3.04 (m, 4H), 1.48 (m, 2H), 1.70 (m, 2H), 1.22 (s, 30H), 0.82 (t, 3H).

MQTS 1142—3.2 mg (9% yield) white solid is obtained. LC/MS calcd [M+H] for $C_{26}H_{54}N_4O_2$: m/z 455; obsd 455 at 13.3 min. $^1$H NMR ($D_2O$, δ): 3.88 (m, 2H), 3.26 (m, 4H), 2.96 (m, 4H), 2.78 (m, 2H), 1.83 (m, 2H), 1.65 (m, 2H), 1.20 (s, 30H), 0.78 (t, 3H).

MQTS 1147—5.9 mg (16% yield) white solid is obtained. LC/MS calcd [M+H] for $C_{27}H_{56}N_4O_2$: m/z 470; obsd 470 at 13.4 min. $^1$H NMR ($D_2O$, δ): 3.81 (s, 2H), 3.24 (t, 2H), 3.02 (m, 2H), 2.94 (t, 4H), 2.42 (t, 2H), 1.96 (m, 2H), 1.82 (m, 2H), 1.66 (m, 2H), 1.15 (s, 30H), 0.76 (t, 3H).

MQTS 1227—6.1 mg (16% yield) white solid is obtained. LC/MS calcd [M+H] for $C_{27}H_{56}N_4O_2$: m/z 469; obsd 469 at 13.3 min. $^1$H NMR ($D_2O$, δ): 3.88 (s, 2H), 3.12 (m, 2H), 2.92 (m, 4H), 1.63 (m, 4H), 1.43 (m, 2H), 1.18 (s, 32H), 0.78 (t, 3H).

MQTS 1232—3.4 mg (9% yield) white solid is obtained. LC/MS calcd [M+H] for $C_{28}H_{58}N_4O_2$: m/z 483; obsd 483 at 13.3 min. $^1$H NMR ($D_2O$, δ): 3.82 (s, 2H), 3.26 (t, 2H), 3.14 (t, 2H), 2.94 (m, 4H), 2.88 (t, 2H), 1.67 (m, 4H), 1.47 (m, 2H), 1.23 (s, 32H), 0.79 (t, 3H).

MQTS 1237—5.3 mg (13% yield) white solid is obtained. LC/MS calcd [M+H] for $C_{29}H_{60}N_4O_2$: m/z 497; obsd 497 at 13.0 min. $^1$H NMR ($D_2O$, δ): 3.83 (s, 2H), 3.17 (m, 2H), 2.94 (m, 4H), 2.43 (m, 2H), 1.96 (m, 2H), 1.64 (m, 4H), 1.51 (m, 2H), 1.34 (m, 4H), 1.24 (s, 30H), 0.80 (t, 3H).

MQTS 2326—8.5 mg (25% yield) white solid is obtained. LC/MS calcd [M+H] for $C_{24}H_{51}N_3O_2$: m/z 414; obsd 414 at 13.5 min. $^1$H NMR ($D_2O$, δ): 3.90 (s, 2H), 3.69 (m, 2H), 3.61 (m, 2H), 3.40 (m, 2H), 3.16 (m, 2H), 3.0 (m, 2H), 1.70 (m, 2H), 1.21 (s, 30H), 0.78 (t, 3H).

MQTS 2328—4.2 mg (12% yield) white solid is obtained. LC/MS calcd [M+H] for $C_{25}H_{53}N_3O_2$: m/z 428; obsd 428 at 13.6 min. $^1$H NMR ($D_2O$, δ): 3.71 (m, 2H), 3.58 (m, 2H), 3.37 (m, 2H), 2.23 (m, 2H), 3.16 (m, 2H), 3.00 (m, 2H), 2.72 (m, 2H), 1.64 (m, 2H), 1.22 (s, 30H), 0.82 (t, 3H).

MQTS 2330—4.9 mg (16% yield) white solid is obtained. LC/MS calcd [M+H] for $C_{26}H_{55}_0N_3O_2$: m/z 442; obsd 442 at 14.7 min. $^1$H NMR ($D_2O$, δ): 3.70 (m, 2H), 3.58 (m, 2H), 3.49 (m, 2H), 3.22 (m, 2H), 3.18 (m, 4H), 2.96 (m, 2H), 2.73 (m, 2H), 1.68 (m, 2H), 1.23 (m, 30H), 0.81 (t, 3H).

Rapid-throughput Fluorescence Displacement Assay for quantifying binding affinities to LPS. The BODIPY-TR-cadaverine (BC; (5-(((4-(4,4-difluoro-5-(2-thienyl)-4-bora-3a, 4a-diaza-s-indacene-3-yl)phenoxy)acetyl)amino)pentylamine, hydrochloride; obtained from Molecular probes, Inc., Eugene, Oreg.) displacement assay to quantify the affinities of binding of compounds to LPS has been described in detail recently.[81] This assay is performed in a rapid-throughput format as follows: the first column (16 wells) of a Corning Nonbinding Surface 384-well flat-bottom black fluorescence microplate contain 15 test compounds plus polymyxin B, all at 5 mM in DMSO, and are serially diluted two-fold in 50 mM Tris buffer, pH 7.4, across the remaining 23 columns, achieving a final dilution of 0.596 nM in a volume of 40 μl. Polymyxin B (PMB), a peptide antibiotic known to bind and neutralize LPS[95] serve as the positive control and reference compound for every plate, enabling the quantitative assessment of repeatability and reproducibility (CV and Z' factors) for the assay. Automated liquid handling is performed on a Precision 2000 automated microplate pipetting system, programmed using the Precision Power software, Bio-Tek Instruments Inc., VT, USA.

Nitric Oxide Assay. Nitric oxide production is measured as total nitrite in murine macrophage J774A.1 cells using the Griess assay[96] as described previously.[94] J774A.1 cells are plated at ~$10^5$/ml in a volume of 40 μl/well, in 384-well, flat-bottomed, cell culture treated microtiter plates and subsequently stimulated with 10 ng/ml lipopolysaccharide (LPS). Concurrent to LPS stimulation, serially diluted concentrations of test compounds are added to the cell medium and left to incubate overnight for 16 h. Polymyxin B is used as reference compound in each plate. Positive- (LPS stimulation only) and negative-controls (J774A.1 medium only) are included in each experiment. Nitrite concentrations are measured by adding 40 μl of supernatant to equal volumes of Griess reagents (50 μl/well; 0.1% NED solution in dd$H_2O$ and 1% sulfanilamide, 5% phosphoric acid solution in dd$H_2O$) and incubating for 15 minutes at room temperature in the dark. Absorbance at 535 nm is measured using a Molecular Devices Spectramax M2 multifunction plate reader (Sunnyvale, Calif.). Nitrite concentrations are interpolated from standard curves obtained from serially diluted sodium nitrite standards.

TABLE 1

Binding affinity (BC displacement; $ED_{50}$) and biological activity (NO inhibition in murine J774 cells; $IC_{50}$) of leads following re-synthesis.

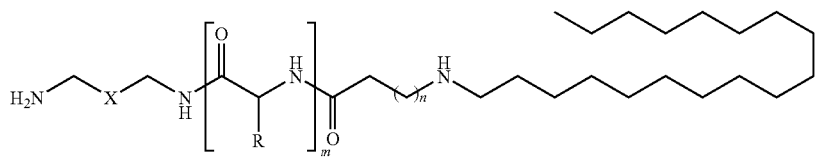

| MQTS | X | m = | R = | n = | $ED_{50}$ value (μM) | $IC_{50}$ value (μM) |
|---|---|---|---|---|---|---|
| 1002 | —$CH_2OCH_2$— | 1 | —$CH_2Ph$ | 0 | 12.4 | 17.6 |
| 1007 | —$CH_2OCH_2$— | 1 | —$CH_2Ph$ | 1 | 2.54 | 2.79 |
| 1012 | —$CH_2OCH_2$— | 1 | —$CH_2Ph$ | 2 | 7.68 | 3.78 |
| 1032 | —$CH_2OCH_2$— | 1 | —$CH_2$-imid | 0 | 13.1 | 1.64 |
| 1037 | —$CH_2OCH_2$— | 1 | —$CH_2$-imid | 1 | 3.17 | 1.88 |
| 1042 | —$CH_2OCH_2$— | 1 | —$CH_2$-imid | 2 | 5.38 | 1.86 |
| 1047 | —$CH_2OCH_2$— | 1 | —H | 0 | 14.0 | 11.5 |
| 1052 | —$CH_2OCH_2$— | 1 | —H | 1 | 14.2 | 1.84 |
| 1057 | —$CH_2OCH_2$— | 1 | —H | 2 | 10.8 | 3.33 |
| 1092 | —$CH_2$— | 1 | —$CH_2Ph$ | 0 | 8.80 | 6.74 |
| 1097 | —$CH_2$— | 1 | —$CH_2Ph$ | 1 | 4.13 | 8.70 |
| 1102 | —$CH_2$— | 1 | —$CH_2Ph$ | 2 | 5.75 | 3.42 |
| 1122 | —$CH_2$— | 1 | —$CH_2$-imid | 0 | 4.87 | 6.90 |
| 1127 | —$CH_2$— | 1 | —$CH_2$-imid | 1 | 6.86 | 8.06 |
| 1132 | —$CH_2$— | 1 | —$CH_2$-imid | 2 | 3.01 | 1.83 |
| 1137 | —$CH_2$— | 1 | —H | 0 | 6.61 | 7.94 |
| 1142 | —$CH_2$— | 1 | —H | 1 | 2420 | 5.26 |
| 1147 | —$CH_2$— | 1 | —H | 2 | 6.14 | 6.57 |
| 1187 | —$CH_2CH_2CH_2$— | 1 | —$CH_2Ph$ | 1 | 3850 | 4.88 |
| 1192 | —$CH_2CH_2CH_2$— | 1 | —$CH_2Ph$ | 2 | 7.51 | 4.80 |
| 1212 | —$CH_2CH_2CH_2$— | 1 | —$CH_2$-imid | 0 | 12.1 | 2.04 |
| 1222 | —$CH_2CH_2CH_2$— | 1 | —$CH_2$-imid | 2 | 18.7 | 0.90 |
| 1227 | —$CH_2CH_2CH_2$— | 1 | —H | 0 | 28.2 | 3.27 |
| 1232 | —$CH_2CH_2CH_2$— | 1 | —H | 1 | 11.2 | 4.61 |
| 1237 | —$CH_2CH_2CH_2$— | 1 | —H | 2 | 9.77 | 3.22 |
| 2322 | —$CH_2$— | 0 | — | 0 | 3.80 | 5.56 |
| 2323 | —$CH_2$— | 0 | — | 1 | 9.92 | 7.49 |
| 2324 | —$CH_2$— | 0 | — | 2 | 6.21 | 4.87 |
| 2325 | —$CH_2CH_2CH_2$— | 0 | — | 0 | 8.74 | 3.96 |
| 2326 | —$CH_2OCH_2$— | 0 | — | 0 | 12.15 | 9.73 |
| 2327 | —$CH_2CH_2CH_2$— | 0 | — | 1 | 4.03 | 1.08 |
| 2328 | —$CH_2OCH_2$— | 0 | — | 1 | 9.16 | 6.54 |
| 2329 | —$CH_2CH_2CH_2$— | 0 | — | 2 | 7.61 | 2.07 |
| 2330 | —$CH_2OCH_2$— | 0 | — | 2 | 5.73 | 5.00 |

Chart 1: Solid-phase Lantern™-based scaffold and combinatorial elements.
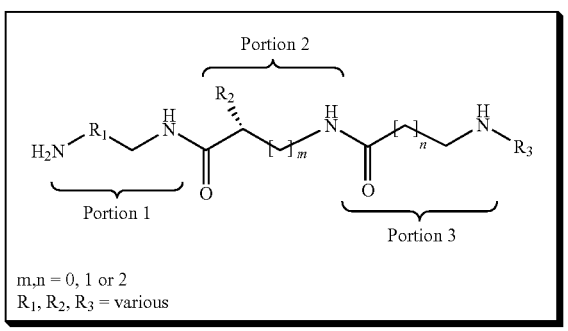
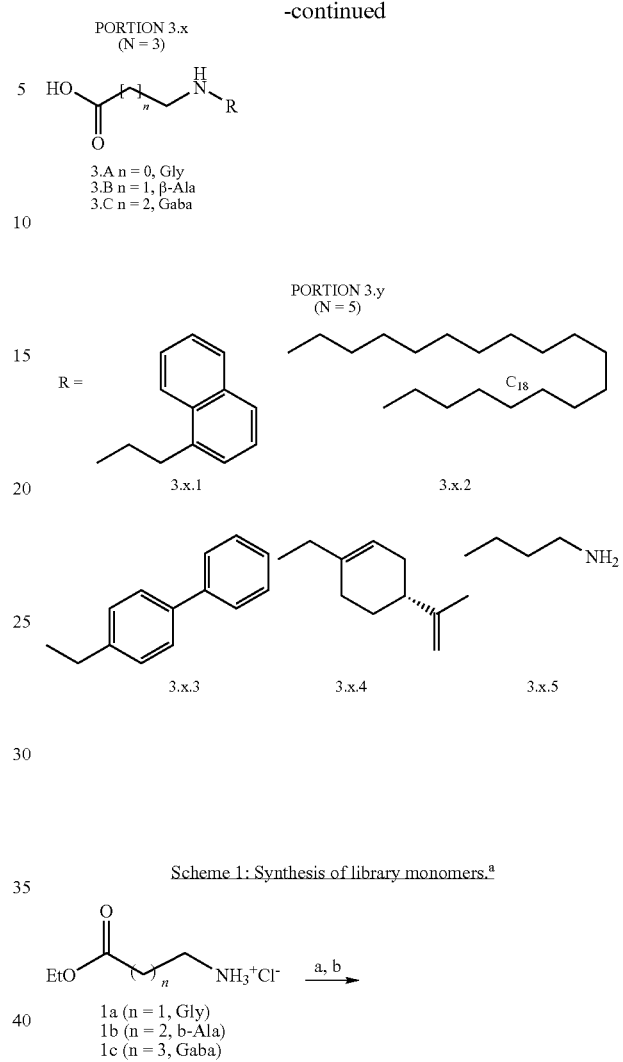
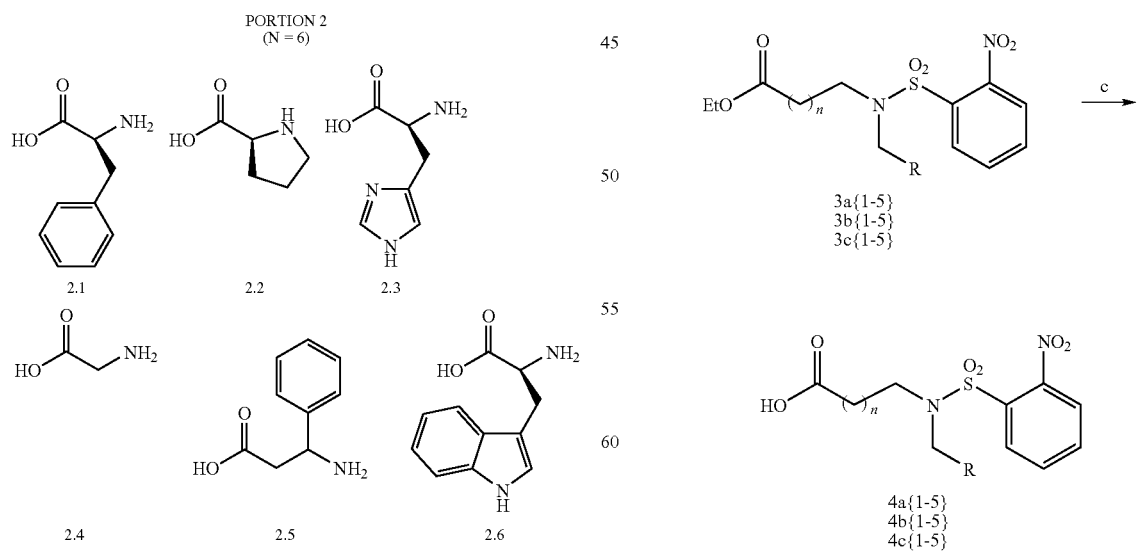

Scheme 2: Synthesis of 15-membered test library.[a]

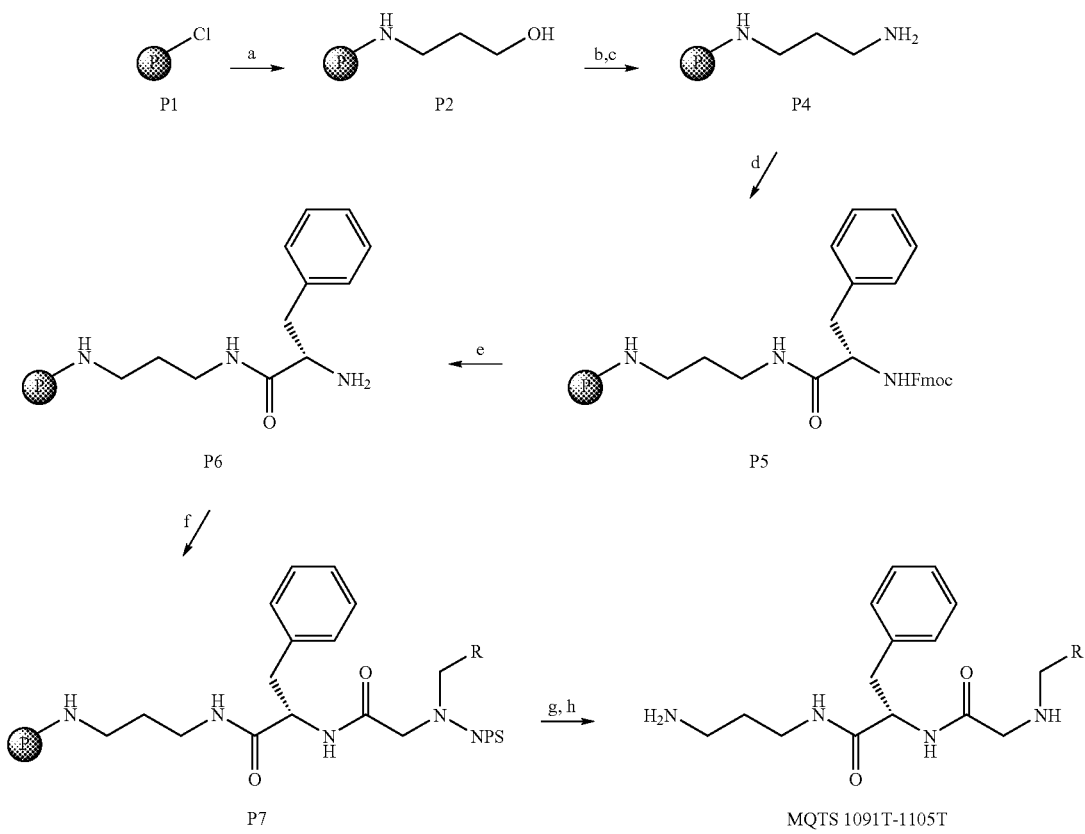

[a]Reagents and conditions: (a) NH$_2$CH$_2$CH$_2$CH$_2$OH excess, CH$_2$Cl$_2$; (b) phthalimide, The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment. The active ingredient can be administered employing a sustained or delayed release delivery system or an immediate release delivery system.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs,* Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouth washes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present invention should be sufficient to affect a therapeutic response in the animal over a reasonable time frame. One skilled in the art will recognize that dosage will depend upon a variety of factors including a condition of the animal, the body weight of the animal, as well as the condition being treated.

A suitable dose is that which will result in a concentration of the active agent in a patient which is known to affect the desired response.

The size of the dose also will be determined by the route, timing and frequency of administration as well as the existence, nature, and extent of any adverse side effects that might accompany the administration of the compound and the desired physiological effect.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or the skill or knowledge of the relevant art. The embodiments described hereinabove are further intended to explain best modes known of practicing the invention and to enable others skilled in the art to utilize the disclosure in such, or other, embodiments and with the various modifications required by the particular applications or uses disclosed herein. Accordingly, the description is not intended to limit the invention to the form disclosed herein. Also, it is intended that the appended claims be construed to include alternative embodiments.

The term "comprising" (and its grammatical variations) as used herein is used in the inclusive sense of "having" or "including" and not in the exclusive sense of "consisting only of".

All publications, patents and patent applications cited in this specification are herein incorporated by reference, and for any and all purposes, as if each individual publication, patent or patent application were specifically and individually indicates to be incorporated by reference. In the case of inconsistencies, the present disclosure will prevail.

REFERENCE LIST

1. Sinnott, M. L. Catalytic mechanism of enzymic glycosyl transfer. *Chem. Rev.* 1990, 90, 1171-1202.
2. Rudd, P. M.; Wormald, M. R.; and Dwek, R. A. Sugar-mediated ligand-receptor interactions in the immune system. *Trends Biotechnol.* 2004, 22, 524-530.
3. Spiro, R. G. Protein glycosylation: nature, distribution, enzymatic formation, and disease implications of glycopeptide bonds. *Glycobiology* 2002, 12, 43R-56R.
4. Varki, A. Biological roles of oligosaccharides: all of the theories are correct. *Glycobiology* 1993, 3, 97-130.
5. Rudd, P. M.; Elliott, T.; Cresswell, P.; Wilson, I. A.; and Dwek, R. A. Glycosylation and the immune system. *Science* 2001, 291, 2370-2376.
6. Sears, P. and Wong, C. H. Intervention of carbohydrate recognition by proteins and nucleic acids. *Proc. Natl. Acad. Sci. U.S.A* 1996, 93, 12086-12093.
7. Klein, E.; Crump, M. P.; and Davis, A. P. Carbohydrate recognition in water by a tricyclic polyamide receptor. *Angew. Chem. Int. Ed Engl.* 2004, 44, 298-302.
8. Lundquist, J. J. and Toone, E. J. The cluster glycoside effect. *Chem. Rev.* 2002, 102, 555-578.
9. Klein, E.; Crump, M. P.; and Davis, A. P. Carbohydrate recognition in water by a tricyclic polyamide receptor. *Angew. Chem. Int. Ed Engl.* 2004, 44, 298-302.
10. Motohiro Nishio, Yoji Umezawa Minoru Hirota and Yasuo Takeuchi. The CH/p interaction: Significance in molecular recognition. *Tetrahedron* 1995, 51(32), 8665-8958.
11. Huang, C-Y.; Cabell, L. A.; Anslyn, E. V. Molecular Recognition of Cyclitols by Neutral Polyaza-Hydrogen-Bonding Receptors: The Strength and Influence of Intramolecular Hydrogen Bonds between Vicinal Alcohols. *J. Am. Chem. Soc.* 1994, 116, 2778-2792.
12. Faham, S.; Hileman, R. E.; Fromm, J. R.; Linhardt, R. J.; and Rees, D. C. Heparin structure and interactions with basic fibroblast growth factor. *Science* 1996, 271, 1116-1120.
13. DiGabriele, A. D.; Lax, I.; Chen, D. I.; Svahn, C. M.; Jaye, M.; Schlessinger, J.; and Hendrickson, W. A. Structure of a heparin-linked biologically active dimer of fibroblast growth factor. *Nature* 1998, 393, 812-817.
14. Fan, Q. R. and Hendrickson, W. A. Structure of human follicle-stimulating hormone in complex with its receptor. *Nature* 2005, 433, 269-277.
15. Honke, K. and Taniguchi, N. Sulfotransferases and sulfated oligosaccharides. *Med. Res. Rev.* 2002, 22, 637-654.
16. Homma, R.; Mase, A.; Toida, T.; Kashiwagi, K.; and Igarashi, K. Modulation of blood coagulation and fibrinolysis by polyamines in the presence of glycosaminoglycans. *Int. J. Biochem. Cell Biol.* 2005.
17. Ratner, D. M.; Adams, E. W.; Disney, M. D.; and Seeberger, P. H. Tools for glycomics: mapping interactions of carbohydrates in biological systems. *Chembiochem.* 2004, 5, 1375-1383.
18. Mechref, Y. and Novotny, M. V. Structural investigations of glycoconjugates at high sensitivity. *Chem. Rev.* 2002, 102, 321-369.
19. Werz, D. B. and Seeberger, P. H. Carbohydrates as the Next Frontier in Pharmaceutical Research. *Chemistry.* 2005, 11, 3194-3206.
20. Powell, A. K.; Yates, E. A.; Fernig, D. G.; and Turnbull, J. E. Interactions of heparin/heparan sulfate with proteins: appraisal of structural factors and experimental approaches. *Glycobiology* 2004, 14, 17R-30R.
21. Blixt, O.; Collins, B. E.; van, d. N., I; Crocker, P. R.; and Paulson, J. C. Sialoside specificity of the siglec family assessed using novel multivalent probes: identification of potent inhibitors of myelin-associated glycoprotein. *J. Biol. Chem.* 2003, 278, 31007-31019.
22. Bryan, M. C.; Plettenburg, O.; Sears, P.; Rabuka, D.; Wacowich-Sgarbi, S.; and Wong, C. H. Saccharide display on microtiter plates. *Chem. Biol.* 2002, 9, 713-720.

23. Smith, E. A.; Thomas, W. D.; Kiessling, L. L.; and Corn, R. M. Surface plasmon resonance imaging studies of protein-carbohydrate interactions. *J. Am. Chem. Soc.* 2003, 125, 6140-6148.

24. Cooper, M. A. Optical biosensors in drug discovery. *Nat. Rev. Drug Discov.* 2002, 1, 515-528.

25. Varenne, A.; Gareil, P.; Colliec-Jouault, S.; and Daniel, R. Capillary electrophoresis determination of the binding affinity of bioactive sulfated polysaccharides to proteins: study of the binding properties of fucoidan to antithrombin. *Anal. Biochem.* 2003, 315, 152-159.

26. Joosten, J. A.; Loimaranta, V.; Appeldoorn, C. C.; Haataja, S.; El Maate, F. A.; Liskamp, R. M.; Finne, J.; and Pieters, R. J. Inhibition of *Streptococcus* suis adhesion by dendritic galabiose compounds at low nanomolar concentration. *J. Med. Chem.* 2004, 47, 6499-6508.

27. Yudovin-Farber, I.; Azzam, T.; Metzer, E.; Taraboulos, A.; and Domb, A. J. Cationic polysaccharides as antiprion agents. *J. Med. Chem.* 2005, 48, 1414-1420.

28. Yudovin-Farber, I.; Azzam, T.; Metzer, E.; Taraboulos, A.; and Domb, A. J. Cationic polysaccharides as antiprion agents. *J. Med. Chem.* 2005, 48, 1414-1420.

29. Supattapone, S.; Wille, H.; Uyechi, L.; Safar, J.; Tremblay, P.; Szoka, F. C.; Cohen, F. E.; Prusiner, S. B.; and Scott, M. R. Branched polyamines cure prion-infected neuroblastoma cells. *J. Virol.* 2001, 75, 3453-3461.

30. Winklhofer, K. F. and Tatzelt, J. Cationic lipopolyamines induce degradation of PrPSc in scrapie-infected mouse neuroblastoma cells. *Biol. Chem.* 2000, 381, 463-469.

31. Supattapone, S.; Nguyen, H. O.; Cohen, F. E.; Prusiner, S. B.; and Scott, M. R. Elimination of prions by branched polyamines and implications for therapeutics. *Proc. Natl. Acad. Sci. U.S.A* 1999, 96, 14529-14534.

32. Castanedo, G. M.; Sailes, F. C.; Dubree, N. J.; Nicholas, J. B.; Caris, L.; Clark, K.; Keating, S. M.; Beresini, M. H.; Chiu, H.; Fong, S.; Marsters, J. C., Jr.; Jackson, D. Y.; and Sutherlin, D. P. Solid-phase synthesis of dual alpha4beta1/alpha4beta7 integrin antagonists: two scaffolds with overlapping pharmacophores. *Bioorg. Med. Chem. Lett.* 2002, 12, 2913-2917.

33. Astles, P. C.; Harris, N. V.; and Morley, A. D. Diamine containing VLA-4 antagonists. *Bioorg. Med. Chem.* 2001, 9, 2195-2202.

34. Ruoslahti, E. and Pierschbacher, M. D. New perspectives in cell adhesion: RGD and integrins. *Science* 1987, 238, 491-497.

35. Lüderitz, O.; Galanos, C.; and Rietschel, E. T. Endotoxins of gram-negative bacteria. *Pharmacol. Ther.* 1982, 15, 383-402.

36. Rietschel, E. T.; Kirikae, T.; Schade, F. U.; Mamat, U.; Schmidt, G.; Loppnow, H.; Ulmer, A. J.; Zähringer, U.; Seydel, U.; Di Padova, F.; and et, a. Bacterial endotoxin: molecular relationships of structure to activity and function. *FASEB J.* 1994, 8, 217-225.

37. Rietschel, E. T.; Brade, L.; Lindner, B.; and Zähringer, U.; Biochemistry of lipopolysaccharides. In *Bacterial endotoxic lipopolysaccharides, vol. I. Molecular biochemistry and cellular biology.* Morrison, D. C. and Ryan, J. L. Eds.; CRC Press: Boca Raton, 1992; pp 1-41.

38. Hurley, J. C. Antibiotic-induced release of endotoxin: A reappraisal. *Clin. Infect. Dis.* 1992, 15, 840-854.

39. Hurley, J. C. Antibiotic-induced release of endotoxin. A therapeutic paradox. *Drug Saf.* 1995, 12, 183-195.

40. Prins, J. M.; van Agtmael, M. A.; Kuijper, E. J.; van Deventer, S. J.; and Speelman, P. Antibiotic-induced endotoxin release in patients with gram-negative urosepsis: a double-blind study comparing imipenem and ceftazidime. *J. Infect. Dis.* 1995, 172, 886-891.

41. Prins, J. M.; Van Deventer, S. J. H.; Kuijper, E. J.; and Speelman, P. Clinical relevance of antibiotic-induced endotoxin release. *Antimicrob. Agents Chemother.* 1994, 38, 1211-1218.

42. Gelfand, J. A. and Shapiro, L. Cytokines and sepsis: pathophysiology and therapy. *New Horizons* 1993, 1, 13-22.

43. Gasche, Y.; Pittet, D.; and Sutter, P. Outcome and prognostic factors in bacteremic sepsis. In *Clinical trials for treatment of sepsis.* Sibbald, W. J. and Vincent, J. L. Eds.; Springer-Verlag: Berlin, 1995; pp 35-51.

44. Centers for Diseases Control. Increases in national hospital discharge survey rates for septicemia—United States, 1979-1987. *MMWR* 1990, 39, 31-34.

45. Martin, G. S.; Mannino, D. M.; Eaton, S.; and Moss, M. The epidemiology of sepsis in the United States from 1979 through 2000. *N. Engl. J. Med.* 2003, 348, 1546-1554.

46. Cross, A. and Opal, S. M. Therapeutic intervention in sepsis with antibody to endotoxin: is there a future? *J. Endotoxin Res.* 1994, 1, 57-59.

47. Ulevitch, R. J. Molecular mechanisms of innate immunity. *Immunol. Res.* 2000, 21, 49-54.

48. Ulevitch, R. J. and Tobias, P. Recognition of gram-negative bacteria and endotoxin by the innate immune system. *Curr. Opin. Immunol.* 1999, 11, 19-23.

49. Dinarello, C. A. Cytokines as mediators in the pathogenesis of septic shock. *Curr. Top. Microbiol. Immunol.* 1996, 216, 133-165.

50. Michie, H. R.; Manogue, K. R.; Spriggs, D. R.; Revhaug, A.; O'Dwyer, S.; Dinarello, C. A.; Cerami, A.; Wolff, S. M.; and Wilmore, D. W. Detection of circulating tumor necrosis factor after endotoxin administration. *N. Engl. J. Med.* 1988, 318, 1481-1486.

51. Meyer, J. and Traber, D. L. Nitric oxide and endotoxin shock. Cardiovasc. *Res.* 1992, 26, 558.

52. Wright, C. E.; Rees, D. D.; and Moncada, S. Protective and pathological roles of nitric oxide in endotoxin shock. *Cardiovasc. Res.* 1992, 26, 48-57.

53. Bone, R. C. The sepsis syndrome. Definition and general approach to management. *Clin. Chest Med.* 1996, 17, 175-181.

54. Raetz, C. R. H. and Whitfield, C. Lipopolysaccharide endotoxins. *Annu. Rev. Biochem.* 2002, 71, 635-700.

55. David, S. A.; Mathan, V. I.; and Balaram, P. Interactions of linear dicationic molecules with lipid A: Structural requisites for optimal binding affinity. *J. Endotoxin. Res.* 1995, 2, 325-336.

56. David, S. A. Towards a rational development of anti-endotoxin agents: novel approaches to sequestration of bacterial endotoxins with small molecules (Invited Review). *J. Molec. Recognition* 2001, 14, 370-387.

57. Behr, J. P.; Demeneix, B.; Loeffler, J. P.; and Perez-Mutul, J. Efficient gene transfer into mammalian primary endocrine cells with lipopolyamine-coated DNA. *Proc. Natl. Acad. Sci. USA* 1989, 86, 6982-6986.
58. Behr, J. P. Gene transfer with synthetic cationic amphiphiles: Prospects for gene therapy. *Bioconjug. Chem.* 1994, 5, 382-389.
59. Felgner, P. L.; Gadek, T. R.; Holm, M.; Roman, R.; Chan, H. W.; Wenz, M.; Northrop, J. P.; Ringold, G. M.; and Danielsen, M. Lipofection: a highly efficient, lipid-mediated DNA transfection procedure. *Proc. Natl. Acad. Sci. USA* 1987, 84, 7413-7417.
60. San, H.; Yang, Z. Y.; Pompili, V. J.; Jaffe, M. L.; Plautz, G. E.; Xu, L.; Felgner, J.; Wheeler, C. J.; Felgner, P. L.; and Gao, X. Safety and short-term toxicity of a novel cationic lipid formulation for human gene therapy. *Hum. Gene Ther.* 1993, 4, 781-788.
61. Miller, K. A.; Suresh Kumar, E. V. K.; Wood, S. J.; Cromer, J. R.; Datta, A.; and David, S. A. Lipopolysaccharide Sequestrants: Structural Correlates of Activity and Toxicity in Novel Acylhomospermines. *J. Med. Chem.* 2005, 48, 2589-2599.
62. Adams, J.; Palombella, V. J.; and Elliott, P. J. Proteasome inhibition: a new strategy in cancer treatment. *Invest. New Drugs* 2000, 18, 109-121.
63. James, T. D.; Sandanayake, K. R. A. S.; and Shinkai, S. Saccharide sensing with molecular receptors based on boronic acid. *Angew. Chem. Int. Ed. Engl.* 1996, 35, 1910-1922.
64. Davis, A. P. and Wareham, R. S. Carbohydrate Recognition through Noncovalent Interactions: A Challenge for Biomimetic and Supramolecular Chemistry. *Angew. Chem. Int. Ed. Engl.* 1998, 38, 2978-2996.
65. Mazik, M.; Bandmann, H.; and Sicking, W. Molecular Recognition of Carbohydrates by Artificial Polypyridine and Polypyrimidine Receptors. *Angew. Chem. Int. Ed. Engl.* 2000, 39, 551-554.
66. Seetharaman, A.; Kanigsberg, A.; Slaaby, R.; Leffler, H.; Barondes, S. H.; and Rini, J. M. X-ray Crystal Structure of the Human Galectin-3 Carbohydrate Recognition Domain at 2.1-Å Resolution. *J. Biol. Chem.* 1998, 273, 13047-13052.
67. Tahirov, T. H.; Lu, T. H.; Liaw, Y. C.; Chen, Y.; and Lin, J. Y. Crystal Structure of Abrin-a at 2.14 Å. *J. Mol. Biol.* 1995, 250, 354-367.
68. Burke, S. D.; Zhao, Q.; Schuster, M. C.; and Kiessling, L. L. Synergistic formation of soluble lectin clusters by a templated multivalent saccharide ligand. *J. Am. Chem. Soc.* 2000, 122, 4518-4519.
69. Elgavish, S. and Shaanan, B. Lectin-carbohydrate interactions: different folds, common recognition principles. *TIBS* 1997, 22, 462-467.
70. Quicho, F. A.; Vyas, N. K.; and Spurlino, J. C. Atomic interactions between proteins and carbohydrates. *Trans. Am. Crystallogr. Assoc.* 1991, 25, 23-35.
71. Kim, E. I.; Paliwal, S.; and Wilcox, C. S. Measurements of molecular electrostatic field effects in edge-to-face aromatic interactions and CH-pi interactions with implications for protein folding and molecular recognition. *J. Am. Chem. Soc.* 1998, 120, 11192-11193.
72. Umezawa, Y. CH/pi interaction in the conformation of organic compounds. A database study. *Tetrahedron* 1999, 55, 10045-10056.
73. Allen, F. H.; Howard, J. A. K.; Hoy, V. J.; Desiraju, G. R.; Reddy, D. S.; and Wilson, C. C. First neutron diffraction analysis of an O—H/pi hydrogen bond: 2-ethynyladamantan-2-ol. *J. Am. Chem. Soc.* 1996, 118, 4081-4084.
74. Steiner, T. and Koellner, G. Hydrogen bonds with pi-acceptors in proteins: Frequencies and role in stabilizing local 3D structures. *J. Mol. Biol.* 2001, 305, 535-557.
75. Hubbard, R. D.; Homer, S. R.; and Miller, B. J. Highly Substituted ter-Cyclopentanes as Receptors for Lipid A. *J. Am. Chem. Soc.* 2001, 123, 5810-5811.
76. Mora, P.; Masip, I.; Cortes, N.; Marquina, R.; Merino, R.; Merino, J.; Carbonell, T.; Mingarro, I.; Messeguer, A.; and Perez-Paya, E. Identification from a positional scanning peptoid library of in vivo active compounds that neutralize bacterial endotoxins. *J. Med. Chem.* 2005, 48, 1265-1268.
77. Ferguson, A. D.; Hofmann, E.; Coulton, J.; Diedrichs, K.; and Welte, W. Siderophore-mediated iron transport: Crystal structure of FhuA with bound lipopolysaccharide. *Science* 1998, 2215-2220.
78. Fukuyama, T.; Jow, C. K.; and Cheung, M. 2- and 4-Nitrobenzenesulfonamides: Exceptionally versatile means for preparation of secondary amines and protection of amines. *Tetrahedron Lett.* 1995, 36, 6373-6374.
79. Fukuyama, T.; Cheung, M.; Jow, C. K.; Hidai, Y.; and Kan, T. 2,4-Dinitrobenzenesulfonamides: A simple and practical method for the preparation of a variety of secondary amines and diamines. *Tetrahedron Lett.* 1997, 38, 5831-5834.
80. Yang, L. and Chiu, K. Solid phase synthesis of Fmoc N-methyl amino acids: Application of the Fukuyama amine synthesis. *Tetrahedron Lett.* 1997, 38, 7307-7310.
81. Wood, S. J.; Miller, K. A.; and David, S. A. Anti-endotoxin agents. 1. Development of a fluorescent probe displacement method for the rapid identification of lipopolysaccharide-binding agents. *Comb. Chem. High. Throughput. Screen.* 2004, 7, 239-249.
82. Wood, S. J.; Miller, K. A.; and David, S. A. Anti-endotoxin agents. 2. Pilot high-throughput screening for novel lipopolysaccharide-recognizing motifs in small molecules. *Comb. Chem. High. Throughput. Screen.* 2004, 7, 733-743.
83. Aoki, H.; Kodama, M.; Tani, T.; and Hanasawa, K. Treatment of sepsis by extracorporeal elimination of endotoxin using polymyxin B-immobilized fiber. *Am. J. Surg.* 1994, 167, 412-417.
84. Bucklin, S. E.; Lake, P.; Logdberg, L.; and Morrison, D. C. Therapeutic efficacy of a polymyxin B-dextran 70 conjugate in experimental model of endotoxemia. *Antimicrob. Agents Chemother.* 1995, 39, 1462-1466.
85. Mayumi, T.; Takezawa, J.; Takahashi, H.; Kuwayama, N.; Fukuoka, T.; Shimizu, K.; Yamada, K.; Kondo, S.; and Aono, K. Low-dose intramuscular polymyxin B improves survival of septic rats. *Shock* 1999, 11, 82-86.
86. Stokes, D. C.; Shenep, J. L.; Fishman, M. L.; Hidner, W. K.; Bysani, G. K.; and Rufus, K. Polymyxin B prevents lipopolysaccharide-induced release of tumor necrosis factor- from alveolar macrophages. *J. Infect. Dis.* 1989, 160, 52-57.

87. David, S. A.; Mathan, V. I.; and Balaram, P. Interactions of linear dicationic molecules with lipid A: Structural features that correspond to optimal binding affinity. *J. Endotoxin. Res.* 1995, 2, 325-336.

88. David, S. A. Towards a rational development of antiendotoxin agents: novel approaches to sequestration of bacterial endotoxins with small molecules. *J. Molec. Recognition* 2001, 14, 370-387.

89. Blagbrough, I. S.; Geall, A. J.; and David, S. A. Lipopolyamines incorporating the teraamine spermine bound to an alkyl chain, sequester bacterial lipopolysaccharide. *Bioorg. Med. Chem. Lett.* 2000, 10, 1959-1962.

90. David, S. A.; Bechtel, B.; Annaiah, C.; Mathan, V. I.; and Balaram, P. Interaction of cationic amphiphilic drugs with lipid A: Implications for development of endotoxin antagonists. *Biochim. Biophys. Acta* 1994, 1212, 167-175.

91. Reyes, C. L. and Chang, G. Structure of the ABC Transporter MsbA in Complex with ADP.Vanadate and Lipopolysaccharide. *Science* 2005, 308, 1031.

92. Goodsell, D. S.; Morris, G. M.; and Olson, A. J. Docking of Flexible Ligands: Applications of AutoDock. *J. Mol. Recognit.* 1996, 9, 1-5.

93. Morris, G. M.; Goodsell, D. S.; Huey, R.; and Olson, A. J. Distributed automated docking of flexible ligands to proteins: Parallel applications of AutoDock 2.4. *J. Comput. -Aid. Molec. Design* 1996, 10, 293-304.

94. David, S. A.; Silverstein, R.; Amura, C. R.; Kielian, T.; and Morrison, D. C. Lipopolyamines: novel antiendotoxin compounds that reduce mortality in experimental sepsis caused by gram-negative bacteria. *Antimicrob. Agents Chemother.* 1999, 43, 912-919.

95. Morrison, D. C. and Jacobs, D. M. Binding of polymyxin B to the lipid A portion of bacterial lipopolysaccharides. *Immunochemistry* 1976, 13, 813-818.

96. Green, L. C.; Wagner, D. A.; Glogowski, J.; Skipper, P. L.; Wishnok, J. S.; and Tannenbaum, S. R. Analysis of nitrate, nitrite and [15-N] nitrate in biological fluids. *Anal. Biochem.* 1982, 126, 131.

What is claimed is:

1. A method for treating a patient suffering from a gram negative bacterial infection or sepsis resulting from a gram negative bacterial infection which comprises administering to said patient an effective amount of a compound selected from the group consisting of:

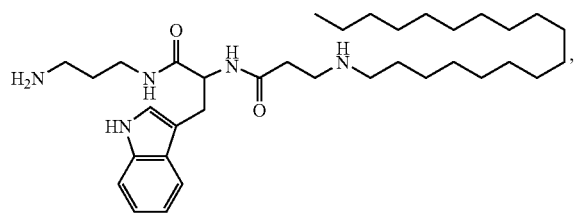

-continued

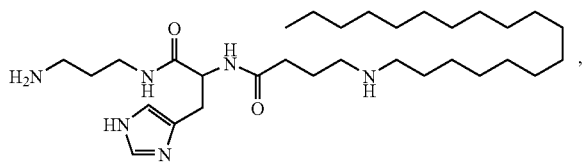

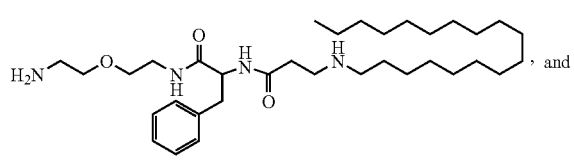

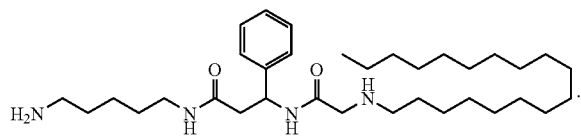

2. The method according to claim 1 wherein said patient is suffering from a gram negative bacterial infection.

3. The method according to claim 1 wherein said patient is suffering from sepsis.

4. The method for treating a patient suffering from a gram negative bacterial infection or sepsis resulting from a gram negative bacterial infection according to claim 1 which comprises administering to said patient an effective amount of a compound represented by the formula:

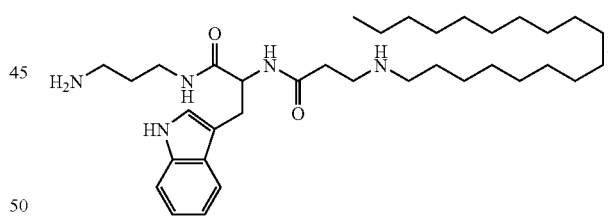

5. The method for treating a patient suffering from a gram negative bacterial infection or sepsis resulting from a gram negative bacterial infection according to claim 1 which comprises administering to said patient an effective amount of a compound represented by the formula:

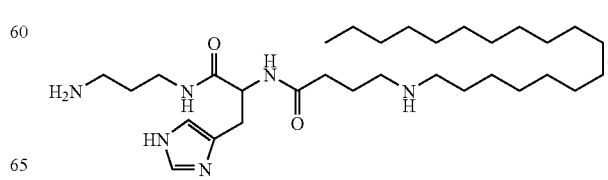

6. The method for treating a patient suffering from a gram negative bacterial infection or sepsis resulting from a gram negative bacterial infection according to claim 1 which comprises administering to said patient an effective amount of a compound represented by the formula:

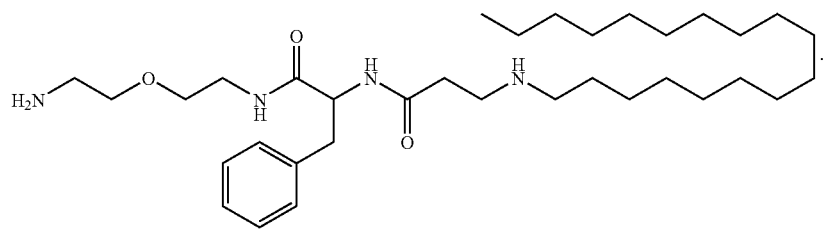

7. The method for treating a patient suffering from a gram negative bacterial infection or sepsis resulting from a gram negative bacterial infection according to claim 1 which comprises administering to said patient an effective amount of a compound represented by the formula:

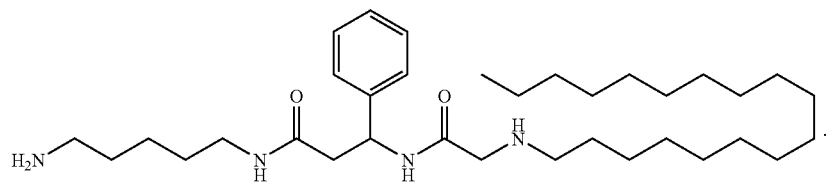

* * * * *

UNITED STATES PATENT AND TRADEMARK OFFICE
CERTIFICATE OF CORRECTION

PATENT NO. : 7,662,999 B2  Page 1 of 1
APPLICATION NO. : 11/693941
DATED : February 16, 2010
INVENTOR(S) : Mark R. Burns et al.

It is certified that error appears in the above-identified patent and that said Letters Patent is hereby corrected as shown below:

Title page insert

--(73) Assignees: MediQuest Therapeutics, Bothell, WA (US) and The University of Kansas, Lawrence, KA (US)-- in lieu of:

(73) Assignees: National Institutes of Health (NIH), Bethesda, MD (US); The United States of America as represented by the Department of Health and Human Services (DHHS), Washington, DC (US); U.S. Government NIH Division of Extramural Inventions and Technology Resources (DEITR).

Signed and Sealed this

Twentieth Day of July, 2010

David J. Kappos
*Director of the United States Patent and Trademark Office*